United States Patent
De Lange et al.

(10) Patent No.: US 11,879,127 B2
(45) Date of Patent: Jan. 23, 2024

(54) METHODS AND COMPOSITIONS FOR EFFICIENT GENETIC MODIFICATIONS OF BACILLUS LICHENIFORMIS STRAINS

(71) Applicant: DANISCO US INC, Palo Alto, CA (US)

(72) Inventors: Dennis De Lange, Leiden (NL); Marc Anton Bernhard Kolkman, Oegstgeest (NL); Frank Wouter Koopman, Utrecht (NL); Chris Leeflang, Twisk (NL)

(73) Assignee: DANISCO US INC., Palo Alto, CA (US)

( * ) Notice: Subject to any disclaimer, the term of this patent is extended or adjusted under 35 U.S.C. 154(b) by 1008 days.

(21) Appl. No.: 16/640,787

(22) PCT Filed: Aug. 21, 2018

(86) PCT No.: PCT/US2018/047194
§ 371 (c)(1),
(2) Date: Feb. 21, 2020

(87) PCT Pub. No.: WO2019/040412
PCT Pub. Date: Feb. 28, 2019

(65) Prior Publication Data
US 2023/0193298 A1  Jun. 22, 2023

Related U.S. Application Data

(60) Provisional application No. 62/549,363, filed on Aug. 23, 2017.

(51) Int. Cl.
*C12N 9/88* (2006.01)
*C12N 15/75* (2006.01)
*C12N 9/04* (2006.01)
*C12N 15/90* (2006.01)
*C12R 1/10* (2006.01)

(52) U.S. Cl.
CPC ........... *C12N 15/75* (2013.01); *C12N 9/0006* (2013.01); *C12N 9/88* (2013.01); *C12N 15/902* (2013.01); *C12R 2001/10* (2021.05); *C12Y 101/01095* (2013.01); *C12Y 401/0102* (2013.01); *C12Y 401/01023* (2013.01)

(58) Field of Classification Search
CPC ........ C12N 9/88; C12N 15/75; C12N 15/902; C07K 14/32
See application file for complete search history.

(56) References Cited

FOREIGN PATENT DOCUMENTS

| WO | 200200907 A1 | 1/2002 |
|---|---|---|
| WO | 2004005525 A2 | 1/2004 |

OTHER PUBLICATIONS

International Search Report and Written Opinion from PCT App. No. PCT/US2018/047194 dated Jan. 29, 2019, 18 pages.
Dong et al., "Current development in genetic engineering strategies of *Bacillus* species", Microbial Cell Factories, vol. 13, No. 1, May 3, 2014, 11 pages.

*Primary Examiner* — Tekchand Saidha

(57) ABSTRACT

The instant disclosure is generally related to compositions and methods for obtaining and constructing *Bacillus licheniformis* host cells (e.g., protein production host cells, cell factories) having increased protein production capabilities. Certain embodiments of the disclosure are directed to efficient genetic modifications of *B. licheniformis* cells and the subsequent selection of such *B. licheniformis* cells having increased protein production capabilities. Certain other embodiments of the disclosure are generally related to methods and compositions for producing/obtaining auxotrophic *B. licheniformis* cells, wherein certain other embodiments of the disclosure are directed to methods and compositions for restoring prototrophy in auxotrophic *B. licheniformis* cells, and expressing genes of interest (GOIs) in such restored prototrophy *B. licheniformis* cells.

3 Claims, 8 Drawing Sheets
Specification includes a Sequence Listing.

Formula I:   [5' HR]—[*lysA*] or [*serA*] or [*pyrF*]—[*GOI* encoding POI]—[3' HR]

Formula II:  [5' HR]—[*GOI* encoding POI]—[*lysA*] or [*serA*] or [*pyrF*]—[3' HR]

*FIG. 7*

Schematic I or

Schematic II or

Schematic III

METHODS AND COMPOSITIONS FOR EFFICIENT GENETIC MODIFICATIONS OF *BACILLUS LICHENIFORMIS* STRAINS

FIELD

The present disclosure is generally related to the fields of bacteriology, microbiology, genetics, molecular biology, enzymology and the like. More particularly, the present disclosure is related to novel methods and compositions for efficient genetic modifications/manipulations in *Bacillus licheniformis* host cells contemplated for use in the production of proteins of interest. Thus, certain embodiments of the disclosure are related to methods and compositions for obtaining auxotrophic *B. licheniformis* cells, whereas certain other embodiments are directed to methods and compositions for restoring prototrophy in these auxotrophic *B. licheniformis* cells and the production of proteins of interest therefrom.

CROSS REFERENCE TO RELATED APPLICATIONS

The present application claims priority to U.S. Provisional Patent Application Ser. No. 62/549,363, filed Aug. 23, 2017, which is incorporated herein by referenced in its entirety.

REFERENCE TO A SEQUENCE LISTING

The contents of the electronic submission of the text file Sequence Listing, named "NB41109-WO-PCT_Sequence-Listing.txt" was created on Jul. 12, 2018 and is 32 KB in size, which is hereby incorporated by reference in its entirety.

BACKGROUND

Gram-positive bacteria such as *Bacillus subtilis, Bacillus licheniformis, Bacillus amyloliquefaciens* and the like are frequently used as microbial factories for the production of industrial relevant proteins, due to their excellent fermentation properties and high yields (e.g., up to 25 grams per liter culture; Van Dijl and Hecker, 2013). For example, *B. subtilis* is well known for its production of α-amylases (Jensen et al., 2000; Raul et al., 2014) and proteases (Brode et al., 1996) necessary for food, textile, laundry, medical instrument cleaning, pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized As Safe" (GRAS) status from the US Food and Drug Administration (Olempska-Beer et al., 2006; Earl et al., 2008; Caspers et al., 2010).

Thus, the production of proteins (e.g., enzymes, antibodies, receptors, etc.) in microbial host cells is of particular interest in the biotechnological arts. Likewise, the optimization of *Bacillus* host cells for the production and secretion of one or more protein(s) of interest is of high relevance, particularly in the industrial biotechnology setting, wherein small improvements in protein yield are quite significant when the protein is produced in large industrial quantities. More particularly, *B. licheniformis* is a *Bacillus* species host cell of high industrial importance, and as such, the ability to genetically modify and engineer *B. licheniformis* host cells for enhanced/increased protein expression/production is highly desirable for construction of new and improved *B. licheniformis* production strains.

Classical strain improvement methods for industrially employed microorganisms have been primarily based on random mutagenesis followed by "selection". The selection methods are typically developed around a suitable assay and are of major importance for selecting wild-type versus mutant (or parental versus daughter) strains. However, it has turned out that these classical methods are limited in their potential for improvement, as consecutive rounds of strain improvement generally yield diminishing increases in yield of desired products, which is at least partially due to the random character of the mutagenesis methods employed. Thus, in addition to the desired mutations, these methods also give rise to mutations which are undesirable and which may negatively influence other characteristics of the strains.

Upon considering the deficiencies of the classical methods of mutagenesis and selection, the implementation of recombinant DNA methods/techniques has been a considerable improvement in the art. For example, recombinant DNA methods/techniques are often used in host strain improvement programs, with the goal of achieving increased expression of desired gene products. The gene products may be proteins (e.g., enzymes) that are of interest themselves, or the encoded gene products may serve as regulatory proteins in the synthesis of other products. Typically, the genes (i.e., encoding the desired gene products) are introduced using vectors (e.g., plasmids, cosmids or phages) that serve as vehicles for introduction of the genes. A particular characteristic of the vector is that when the expression product cannot be easily selected based on an altered phenotypic property, the vector is generally equipped with a marker that can be easily selected. In addition, widespread use and the subsequent spreading of specific marker genes has recently become a debatable topic. More specifically, the use of antibiotics and antibiotic selection markers may give rise to an undesired spread of strains that have become antibiotic resistant, thereby potentially necessitating the continued development of novel, ever more potent antibiotics. It is therefore not surprising that there is a general tendency in the art to use recombinant microorganisms containing no antibiotic resistance genes, or more generally, as little as possible of foreign DNA. Ideally the transformed microorganism would contain only the desired gene(s), fragments thereof, or modifications in the gene, and as little as possible or no further remnants of the DNA used for cloning.

The present disclosure is generally related to the highly desirable and unmet needs for obtaining and constructing *Bacillus licheniformis* host cells (e.g., protein production host cells, cell factories) having increased protein production capabilities. More particularly, the present disclosure addresses ongoing and unmet needs in the biotechnological arts for efficient and reliable genetic modifications/manipulations of *Bacillus licheniformis* cells and the subsequent selection of such *Bacillus licheniformis* cells having increased protein production capabilities.

SUMMARY

The instant disclosure is generally related to compositions and methods for obtaining and constructing *Bacillus licheniformis* host cells (e.g., protein production host cells, cell factories) having increased protein production capabilities. More particularly, the present disclosure is directed to efficient genetic modifications of *Bacillus licheniformis* cells and the subsequent selection of such *Bacillus licheniformis* cells having increased protein production capabilities. Thus, certain embodiments of the disclosure are generally related to methods and compositions for producing/obtaining auxotrophic *B. licheniformis* cells, wherein certain other embodiments of the disclosure are directed to methods and compositions for restoring prototrophy in auxotrophic *B. licheniformis* cells.

For example, certain embodiments of the disclosure are related to lysine auxotrophic *B. licheniformis* cells comprising an inactivated genomic diaminopimelate decarboxylase (lysA) gene, serine auxotrophic *B. licheniformis* cells comprising an inactivated genomic D-3-phosphoglycerate dehydrogenase (serA) gene, uracil auxotrophic *B. licheniformis* cells comprising an inactivated genomic orotidine 5'-phosphate decarboxylase (pyrF) gene and *B. licheniformis* cells comprising combinations thereof.

Certain other embodiments are directed to compositions and methods for concurrently introducing a recombinant DNA construct into an auxotrophic *B. licheniformis* host cell (e.g., a *B. licheniformis* lysine auxotrophic cell, a *B. licheniformis* serine auxotrophic cell, a *B. licheniformis* uracil auxotrophic cell and combinations thereof) and restoring prototrophy in the *B. licheniformis* auxotrophic host cell, wherein the DNA construct comprises at least a nucleic acid sequence encoding a selectable marker (e.g., a LysA polypeptide, a SerA polypeptide, a PyrF polypeptide and combinations thereof) operably linked to a nucleic acid sequence encoding a polypeptide of interest (e.g., an amylase, a protease and the like).

Thus, in certain embodiments, the disclosure is directed to a method for introducing a recombinant DNA construct into a modified *Bacillus licheniformis* host cell, the method comprising (a) providing a modified *B. licheniformis* host cell comprising an inactivated genomic diaminopimelate decarboxylase (lysA) gene, (b) introducing into the modified cell a recombinant DNA construct comprising a selectable marker encoding a diaminopimelate decarboxylase (LysA) protein, (c) cultivating the host cell of step (b) in a growth-medium which does not comprise lysine, and (d) selecting a host cell comprising the DNA construct that is capable of growing in the medium of step (c).

In another embodiment, the disclosure is related to a method for introducing a recombinant DNA construct into a modified *Bacillus licheniformis* host cell, the method comprising (a) providing a modified *B. licheniformis* host cell comprising an inactivated genomic D-3-phosphoglycerate dehydrogenase (serA) gene, (b) introducing into the modified cell a recombinant DNA construct comprising a selectable marker encoding a D-3-phosphoglycerate dehydrogenase (SerA) protein, (c) cultivating the host cell of step (b) in a growth-medium which does not comprise serine, and (d) selecting a host cell comprising the DNA construct that is capable of growing in the medium of step (c).

In other embodiments, the disclosure is related to a method for introducing a recombinant DNA construct into a modified *Bacillus licheniformis* host cell, the method comprising: (a) providing a modified *B. licheniformis* host cell comprising an inactivated genomic orotidine 5'-phosphate decarboxylase (pyrF) gene, (b) introducing into the modified cell a recombinant DNA construct comprising a selectable marker encoding a orotidine 5'-phosphate decarboxylase (PyrF) protein, (c) cultivating the host cell of step (b) in a growth-medium which does not comprise uracil, and (d) selecting a host cell comprising the DNA construct that is capable of growing in the medium of step (c).

In certain embodiments, the introduced recombinant DNA construct is circular DNA or linear DNA. In certain other embodiments of the methods, the DNA construct comprises an upstream (5') nucleic acid sequence homology region (5'-HR) or downstream (3') nucleic acid sequence homology region (3'-HR) sufficiently homologous with a genomic region (locus) of the host cell to effect integration into the genome by homologous recombination. In another embodiment of the methods, the DNA construct comprises an upstream (5') nucleic acid sequence homology region (5'-HR) and a downstream (3') nucleic acid sequence homology region (3'-HR), wherein the 5'-HR and 3'-HR are sufficiently homologous with a genomic region (locus) of the host cell to effect integration into the genome by homologous recombination.

In yet other embodiments of the methods, the DNA construct further comprises a downstream (3') nucleic acid sequence encoding a polypeptide of interest (POI) or an upstream (5') nucleic acid sequence encoding a polypeptide of interest (POI), wherein the polynucleotide construct comprises Formula (I) or Formula (II), respectively, in the 5' to 3' direction:

[5' HR]-[lysA] or [serA] or [pyrF]-[GOI encoding POI]-[3' HR]   (I)

[5' HR]-[GOI encoding POI]-[lysA] or [serA] or [pyrf]-[3' HR]   (II)

wherein the 5'-HR and 3'-HR are sufficiently homologous with a genomic region (locus) of the host cell to effect integration into the genome by homologous recombination. In certain embodiments, the POI encoded by the GOI is selected from the group consisting of acetyl esterases, aryl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, polyesterases, phenoloxidases, phytases, polygalacturonases, proteases, peptidases, rhamno-galacturonases, ribonucleases, transferases, transport proteins, transglutaminases, xylanases, hexose oxidases, and combinations thereof. In certain other embodiments, the POI is an amylase or a protease.

In other embodiments of the methods, the genomic lysA gene encodes a LysA protein comprising an amino acid sequence at least 95% identical to SEQ ID NO: 2. In other embodiments, the genomic lysA gene comprises a nucleotide sequence of SEQ ID NO: 1 (or a degenerate sequence thereof) encoding a LysA protein of SEQ ID NO: 2. In certain other embodiments, a *B. licheniformis* genomic lysA gene comprises a nucleotide sequence encoding a LysA protein comprising at least 90% sequence identity to the LysA protein of SEQ ID NO: 2, wherein a LysA protein having at least 90% sequence identity to SEQ ID NO: 2 comprises diaminopimelate decarboxylase activity. In certain other embodiments, a *B. licheniformis* genomic lysA gene encodes a LysA protein having at least 80% sequence identity to SEQ ID NO: 2, with the proviso that such *B. licheniformis* host cells comprising a genomic lysA gene encoding a LysA protein having at least 80% sequence identity to SEQ ID NO: 2 comprise sufficient diaminopimelate decarboxylase activity that the *B. licheniformis* host cells are capable of growing in a growth medium which does not require or comprise lysine.

In other embodiments of the methods, the genomic serA gene encodes a SerA protein comprising an amino acid sequence at least 95% identical to SEQ ID NO: 28. In other embodiments, the genomic serA gene comprises a nucleotide sequence of SEQ ID NO: 27 (or a degenerate sequence thereof) encoding a SerA protein of SEQ ID NO: 28. In certain other embodiments, a *B. licheniformis* genomic serA gene comprises a nucleotide sequence encoding a SerA protein comprising at least 90% sequence identity to the SerA protein of SEQ ID NO: 28, wherein a SerA protein having at least 90% sequence identity to SEQ ID NO: 28 comprises D-3-phosphoglycerate dehydrogenase activity. In certain other embodiments, a *B. licheniformis* genomic serA gene encodes a SerA protein having at least 80% sequence identity to SEQ ID NO: 28, with the proviso that such *B. licheniformis* host cells comprising a genomic serA gene encoding a SerA protein having at least 80% sequence identity to SEQ ID NO: 28 comprise sufficient D phosphoglycerate dehydrogenase activity that the *B. licheniformis* host cells are capable of growing in a growth medium which does not require or comprise serine.

In other embodiments of the methods, the genomic pyrF gene encodes a PyrF protein comprising an amino acid sequence at least 95% identical to SEQ ID NO: 66. In other embodiments, the genomic pyrF gene comprises a nucleotide sequence of SEQ ID NO: 65 (or a degenerate sequence thereof) encoding a PyrF protein of SEQ ID NO: 68. In certain other embodiments, a *B. licheniformis* genomic pyrF gene comprises a nucleotide sequence encoding a PyrF protein comprising at least 90% sequence identity to the PyrF protein of SEQ ID NO: 66, wherein a PyrF protein having at least 90% sequence identity to SEQ ID NO: 66 comprises orotidine 5'-phosphate decarboxylase activity. In certain other embodiments, a *B. licheniformis* genomic pyrF gene encodes a PyrF protein having at least 80% sequence identity to SEQ ID NO: 66, with the proviso that such *B. licheniformis* host cells comprising a genomic pyrF gene encoding a PyrF protein having at least 80% sequence identity to SEQ ID NO: 66 comprise sufficient orotidine 5'-phosphate decarboxylase activity that the *B. licheniformis* host cells are capable of growing in a growth medium which does not require or comprise uracil.

In certain other embodiments of the methods, the modified *B. licheniformis* host cell of step (a) comprises a plasmid encoding a comK polypeptide (SEQ ID NO: 68). In particular embodiments, the plasmid encoding comK is plasmid pBLcomK, which is further detailed in FIG. 2.

In certain other embodiments, the disclosure is directed to methods for introducing (e.g., transforming) at least two recombinant DNA constructs encoding the same protein of interest (POI) (or different proteins of interest) into different chromosomal loci of a modified *Bacillus licheniformis* host cell, the method comprising (a) providing a modified *B. licheniformis* cell comprising at least two inactivated *B. licheniformis* chromosomal genes selected from the group consisting of an inactivated genomic diaminopimelate decarboxylase (lysA) gene, an inactivated genomic D-3-phosphoglycerate dehydrogenase (serA) gene and an inactivated genomic orotidine 5'-phosphate decarboxylase (pyrF) gene, (b) introducing into the modified cell of step (a) at least two recombinant DNA constructs encoding the at least two inactivated *B. licheniformis* chromosomal genes, wherein the DNA constructs comprise Formulae (i)-(iii):

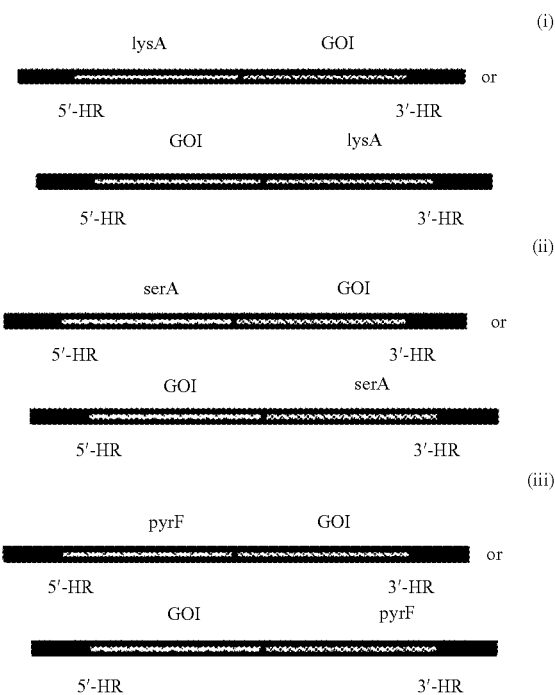

wherein the lysA nucleic acid sequence encodes a diaminopimelate decarboxylase (LysA) protein, the serA nucleic acid sequence encodes a D-3-phosphoglycerate dehydrogenase (SerA) protein, the pyrF nucleic acid sequence encodes a orotidine 5'-phosphate decarboxylase (PyrF) protein, the GOI nucleic acid sequence encodes a protein of interest (POI), and the 5'-homology region (5'-HR) and 3'-homology region (3'-HR) comprise nucleic acid sequences sufficiently homologous with a genomic (chromosomal) region (locus) of the host cell to effect integration into the genome by homologous recombination, (c) cultivating the host cell of step (b) in a growth-medium which does not comprise lysine, serine or uracil, and (d) selecting a host cell comprising the DNA constructs that is capable of growing in the medium of step (c). Thus, in certain embodiments, the DNA constructs of Formulae (i)-(iii) encode the same POI, and in other embodiments, the DNA constructs of Formulae (i)-(iii) each encode a different POI. In other embodiments, the DNA constructs are circular DNA or linear DNA.

In another embodiment of the methods, the DNA construct of Formula (i) comprises a 5'-HR and 3'-HR sufficiently homologous with a genomic (chromosomal) region (locus) of the host cell to effect integration into the genomic (chromosomal) locus by homologous recombination, the DNA construct of formula (ii) comprises a 5'-HR and 3'-HR sufficiently homologous with a genomic (chromosomal) region (locus) of the host cell to effect integration into the genomic (chromosomal) locus by homologous recombination and the DNA construct of Formula (iii) comprises a 5'-HR and 3'-HR sufficiently homologous with a genomic (chromosomal) region (locus) of the host cell to effect integration into the genomic (chromosomal) locus by homologous recombination.

In other embodiments, the DNA construct of Formula (i) comprises a 5'-HR and 3'-HR sufficiently homologous with a genomic (chromosomal) region (locus) of the lysA gene of the host cell to effect integration into the genomic lysA locus by homologous recombination. In another embodiment, the DNA construct of Formula (ii) comprises a 5'-HR and 3'-HR sufficiently homologous with a genomic region (locus) of the serA gene of the host cell to effect integration into the genomic serA locus by homologous recombination. In yet other embodiments, the DNA construct of Formula (iii) comprises a 5'-HR and 3'-HR sufficiently homologous with a genomic region (locus) of the pyrF gene of the host cell to effect integration into the genomic pyrF locus by homologous recombination.

In other embodiments of the methods, the POI is selected from the group consisting of acetyl esterases, aryl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, polyesterases, phenoloxidases, phytases, polygalacturonases, proteases, peptidases, rhamno-galacturonases, ribonucleases, transferases, transport proteins, transglutaminases, xylanases, hexose oxidases, and combinations thereof. In particular embodiments, the POI is an amylase, a protease or a combination thereof.

In other embodiments of the methods, the genomic lysA gene encodes a LysA protein comprising an amino acid sequence at least 90% identical to SEQ ID NO: 2. In another embodiment, the genomic serA gene encodes a SerA protein comprising an amino acid sequence at least 90% identical to SEQ ID NO: 28. In other embodiments, the genomic pyrF gene encodes a PyrF protein comprising an amino acid sequence at least 90% identical to SEQ ID NO: 66.

In another embodiment, the disclosure is directed to modified *Bacillus licheniformis* host cells produced according to the methods herein.

In other embodiments, the disclosure is related to recombinant DNA constructs introduced into a modified (auxotrophic) *Bacillus licheniformis* host cell. For example, certain embodiments of the disclosure are related to a recombinant DNA construct introduced into a modified *Bacillus licheniformis* host cell (i.e., a lysine auxotroph comprising an inactivated genomic diaminopimelate decarboxylase (lysA) gene), wherein the DNA construct comprises Formula (i):

wherein the lysA gene encodes a LysA protein comprising an amino acid sequence at least 90% identical to SEQ ID NO: 2, wherein the DNA construct encoding the lysA gene and the GOI comprises an upstream (5') nucleic acid sequence homology region (5'-HR) and downstream (3') nucleic acid sequence homology region (3'-HR) operably linked, wherein the 5'-HR and the 3'-HR comprise sufficient homology with a genomic region (locus) of the host cell to effect integration of the DNA construct into the genomic locus by homologous recombination. In other embodiments, the 5'-HR and the 3'-HR comprise sufficient homology to a genomic (chromosomal) lysA (locus) of the *B. licheniformis* host cell to effect integration of the DNA construct into the chromosomal lysA locus by homologous recombination.

In other embodiments, the disclosure is related to a recombinant DNA construct introduced into a modified *Bacillus licheniformis* host cell (i.e., a serine auxotroph comprising an inactivated genomic D phosphoglycerate dehydrogenase (serA) gene), wherein the DNA construct comprises Formula (ii):

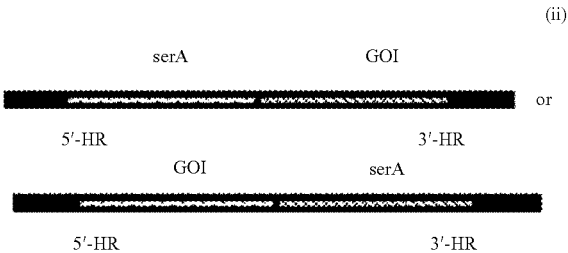

wherein the serA gene encodes a SerA protein comprising an amino acid sequence at least 90% identical to SEQ ID NO: 28, wherein the DNA construct encoding the serA gene and the GOI comprises an upstream (5') nucleic acid sequence homology region (5'-HR) and downstream (3') nucleic acid sequence homology region (3'-HR) operably linked, wherein the 5'-HR and the 3'-HR comprise sufficient homology with a genomic region (locus) of the host cell to effect integration of the DNA construct into the genomic locus by homologous recombination. In other embodiments, the 5'-HR and the 3'-HR comprise sufficient homology to a genomic (chromosomal) serA (locus) of the *B. licheniformis* host cell to effect integration of the DNA construct into the chromosomal serA locus by homologous recombination.

In another embodiment, the disclosure is related to a recombinant DNA construct introduced into a modified *Bacillus licheniformis* host cell (i.e., an uracil auxotroph comprising an inactivated genomic orotidine 5'-phosphate decarboxylase (pyrF) gene), wherein the DNA construct comprises Formula (iii):

wherein the pyrF gene encodes a PyrF protein comprising an amino acid sequence at least 90% identical to SEQ ID NO: 66, wherein the DNA construct encoding the pyrF gene and the GOI comprises an upstream (5') nucleic acid sequence homology region (5'-HR) and downstream (3') nucleic acid sequence homology region (3'-HR) operably linked, wherein the 5'-HR and the 3'-HR comprise sufficient homology with a genomic region (locus) of the host cell to effect integration of the DNA construct into the genomic locus by homologous recombination. In other embodiments, the 5'-HR and the 3'-HR comprise sufficient homology to a genomic (chromosomal) pyrF (locus) of the *B. licheniformis* host cell to effect integration of the DNA construct into the chromosomal pyrF locus by homologous recombination.

In certain other embodiments, the disclosure is directed to a lysine auxotrophic *B. licheniformis* (daughter) cell derived from a prototrophic *B. licheniformis* (parental) cell, wherein the *B. licheniformis* (daughter) cell comprises a genetic modification which disrupts, deletes or down-regulates an endogenous *B. licheniformis* diaminopimelate decarboxylase (lysA) gene encoding a LysA protein comprising at least 90% sequence identity to the SEQ ID NO: 1. Certain other embodiments are directed to a serine auxotrophic *B. licheniformis* (daughter) cell derived from a prototrophic *B. licheniformis* (parental) cell, wherein the *B. licheniformis* (daughter) cell comprises a genetic modification which disrupts, deletes or down-regulates an endogenous *B. licheniformis* D-3-phosphoglycerate dehydrogenase (serA) gene encoding a SerA protein comprising at least 90% sequence identity to the SEQ ID NO: 28. In another embodiment, the disclosure is related to a uracil auxotrophic *B. licheniformis* (daughter) cell derived from a prototrophic *B. licheniformis* (parental) cell, wherein the *B. licheniformis* (daughter) cell comprises a genetic modification which disrupts, deletes or down-regulates an endogenous *B. licheniformis* orotidine 5'-phosphate decarboxylase (pyrF) gene encoding a PyrF protein comprising at least 90% sequence identity to the SEQ ID NO: 66.

In certain other embodiments, the disclosure is directed to an auxotrophic *B. licheniformis* (daughter) cell derived from a prototrophic *B. licheniformis* (parental) cell, wherein the *B. licheniformis* (daughter) cell comprises a genetic modification which disrupts, deletes or down-regulates at least two endogenous *B. licheniformis* genes selected from the group consisting of a diaminopimelate decarboxylase (lysA) gene, a D-3-phosphoglycerate dehydrogenase (serA) gene and a orotidine 5'-phosphate decarboxylase (pyrF) gene. In certain other embodiments, the disclosure is directed to an auxotrophic *B. licheniformis* (daughter) cell derived from a prototrophic *B. licheniformis* (parental) cell, wherein the *B. licheniformis* (daughter) cell comprises a genetic modification which disrupts, deletes or down-regulates an endogenous *B. licheniformis* diaminopimelate decarboxylase (lysA) gene, a D-3-phosphoglycerate dehydrogenase (serA) gene and a orotidine 5'-phosphate decarboxylase (pyrF) gene.

In another embodiment, the disclosure is related to such lysine auxotrophic *B. licheniformis* (daughter) cells (i.e., derived from prototrophic *B. licheniformis* parental cells), wherein prototrophy of the (lysine auxotrophic) *B. licheniformis* (daughter) cells is restored by introducing (e.g., transforming) into the auxotrophic daughter cell a recombinant DNA construct comprising Formula (i):

(i)

lysA        GOI

▬▬▬▬▬▬▬▬▬▬▬▬▬▬▬▬▬▬▬  or

5'-HR            3'-HR

-continued

GOI        lysA

▬▬▬▬▬▬▬▬▬▬▬▬▬▬▬▬▬▬▬

5'-HR            3'-HR wherein (a) the 5' nucleic acid sequence homology region (5'-HR) comprises homology to an upstream (5') genomic (chromosomal) sequence of the *B. licheniformis* daughter cell, (b) the 3' nucleic acid sequence homology region (3'-HR) comprises homology to a downstream (3') genomic (chromosomal) sequence of the *B. licheniformis* daughter cell, (c) the lysA gene is a nucleic acid sequence encoding a functional LysA protein comprising at least 90% sequence identity to SEQ ID NO: 2, and (d) the GOI is a nucleic acid sequence encoding a protein of interest (POI), wherein the 5'-HR and 3'-HR comprise sufficient homology to a genomic (chromosomal) locus in the auxotrophic *B. licheniformis* (daughter) cell to effect integration of the DNA construct into the genomic (chromosomal) locus of the auxotrophic *B. licheniformis* (daughter) cell by homologous recombination, wherein homologous integration of the DNA constructs restores the prototrophy of the *B. licheniformis* host cell.

In another embodiment, the disclosure is related to such serine auxotrophic *B. licheniformis* (daughter) cells (i.e., derived from prototrophic *B. licheniformis* parental cells), wherein prototrophy of the (serine auxotrophic) *B. licheniformis* (daughter) cells is restored by introducing (e.g., transforming) into the auxotrophic daughter cell a recombinant DNA construct comprising Formula (i):

(i)

serA        GOI

▬▬▬▬▬▬▬▬▬▬▬▬▬▬▬▬▬▬▬  or

5'-HR            3'-HR

GOI        serA

▬▬▬▬▬▬▬▬▬▬▬▬▬▬▬▬▬▬▬

5'-HR            3'-HR wherein (a) the 5' nucleic acid sequence homology region (5'-HR) comprises homology to an upstream (5') genomic (chromosomal) sequence of the *B. licheniformis* daughter cell, (b) the 3' nucleic acid sequence homology region (3'-HR) comprises homology to a downstream (3') genomic (chromosomal) sequence of the *B. licheniformis* daughter cell, (c) the serA gene is a nucleic acid sequence encoding a functional SerA protein comprising at least 90% sequence identity to SEQ ID NO: 28, and (d) the GOI is a nucleic acid sequence encoding a protein of interest (POI), wherein the 5'-HR and 3'-HR comprise sufficient homology to a genomic (chromosomal) locus in the auxotrophic *B. licheniformis* (daughter) cell to effect integration of the DNA construct into the genomic (chromosomal) locus of the auxotrophic *B. licheniformis* (daughter) cell by homologous recombination, wherein homologous integration of the DNA constructs restores the prototrophy of the *B. licheniformis* host cell.

In another embodiment, the disclosure is related to such uracil auxotrophic *B. licheniformis* (daughter) cells (i.e., derived from prototrophic *B. licheniformis* parental cells), wherein prototrophy of the (uracil auxotrophic) *B. licheniformis* (daughter) cells is restored by introducing (e.g., transforming) into the auxotrophic daughter cell a recombinant DNA construct comprising Formula (iii):

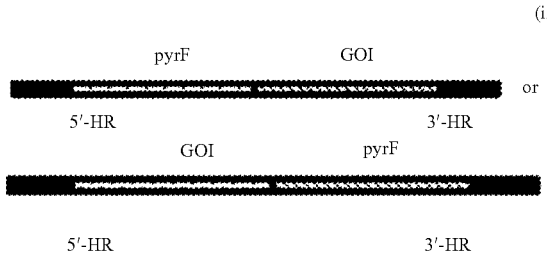

wherein (a) the 5' nucleic acid sequence homology region (5'-HR) comprises homology to an upstream (5') genomic (chromosomal) sequence of the *B. licheniformis* daughter cell, (b) the 3' nucleic acid sequence homology region (3'-HR) comprises homology to a downstream (3') genomic (chromosomal) sequence of the *B. licheniformis* daughter cell, (c) the pyrF gene is a nucleic acid sequence encoding a functional PyrF protein comprising at least 90% sequence identity to SEQ ID NO: 66, and (d) the GOI is a nucleic acid sequence encoding a protein of interest (POI), wherein the 5'-HR and 3'-HR comprise sufficient homology to a genomic (chromosomal) locus in the auxotrophic *B. licheniformis* (daughter) cell to effect integration of the DNA construct into the genomic (chromosomal) locus of the auxotrophic *B. licheniformis* (daughter) cell by homologous recombination, wherein homologous integration of the DNA constructs restores the prototrophy of the *B. licheniformis* host cell.

In yet other embodiments, the disclosure is directed to auxotrophic *B. licheniformis* cells having improved genetic competency (e.g., increased transformation efficiency), thereby leading to a higher frequency of transformed cells thereof. For example, in certain embodiments, the disclosure is related to auxotrophic *B. licheniformis* cells transformed with a linear DNA fragment (i.e., a DNA construct) comprising a selectable marker of the disclosure (e.g., lysA, serA, pyrF). More particularly, as described herein, such auxotrophic *B. licheniformis* cells transformed with a linear DNA fragment comprising a selectable marker of the disclosure have a significant improvement in transformation efficiency relative to (parental) *B. licheniformis* cells transformed with a linear DNA fragment comprising an antibiotic marker (e.g., a chloramphenicol marker). Thus, in particular embodiments, the disclosure is related to such auxotrophic *B. licheniformis* cells comprising an increased/improved transformation efficiency, which auxotrophic *B. licheniformis* cells are derived from (parental) prototrophic *B. licheniformis* cells.

Thus, certain other embodiments of the disclosure are related to methods and compositions for obtaining or producing auxotrophic *B. licheniformis* cells, methods and compositions for restoring prototrophy in such auxotrophic *B. licheniformis* cells, the proteins of interest (POIs) produced from such restored prototrophy *B. licheniformis* cells, and the modified *B. licheniformis* cells derived therefrom and methods of making and using the same.

BRIEF DESCRIPTION OF DRAWINGS

FIG. 7 presents DNA constructs of Formula I and Formula II, wherein "[5' HR]" and "[3' HR]" are (*B. licheniformis*) 5' and 3' homology regions, "[lysA]" or "[serA]" or "[pyrF]" indicate genes encoding selectable markers LysA, SerA and PyrF, respectively, and "[GOI encoding POI]" indicates a gene of interest encoding a protein of interest. The "or" separating the selectable marker genes "[lysA] or [serA] or [pyrF]" indicates the option of using any one of the selectable markers presented.

BRIEF DESCRIPTION OF THE BIOLOGICAL SEQUENCES

Figure 1:
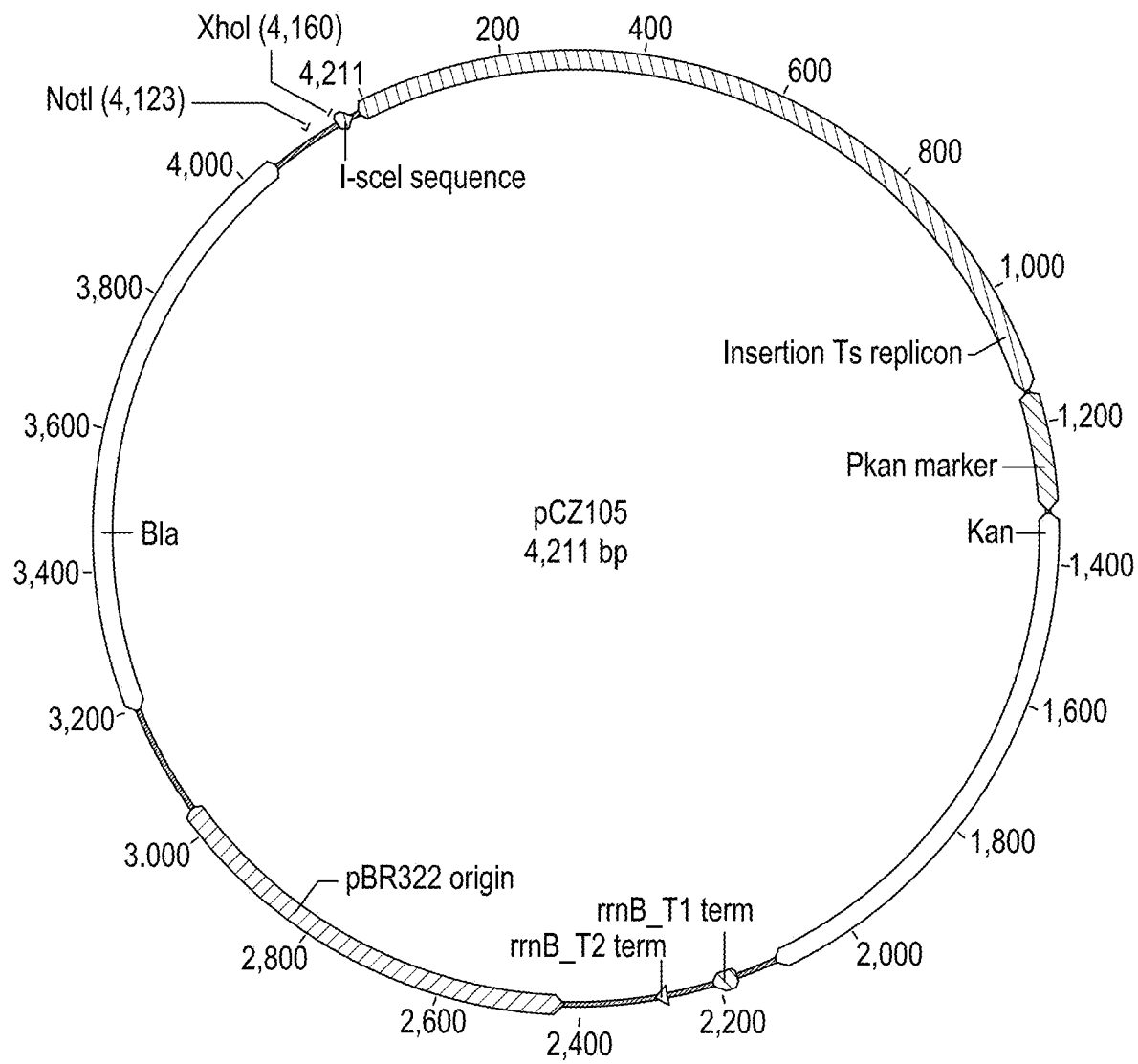
FIG. 1 shows a plasmid map of vector pCZ105, containing various restriction enzyme (RE) sites, amongst which are the RE sites XhoI and NotI. Also comprised in plasmid vector pCZ105 is a pE194 temperature sensitive replicon (Ts replicon), a kanamycin coding sequence (Kan), a kanamycin promoter (pKan marker), a ribosomal terminator sequence (Term rrnB), a β-lactamase ("bla") gene, an I-Sce site and a pBR322 origin of replication.

SEQ ID NO: 1 is a nucleic acid sequence encoding a *B. licheniformis* diaminopimelate decarboxylase (LysA) polypeptide of SEQ ID NO: 2.

SEQ ID NO: 2 is the amino acid sequence of a *B. licheniformis* diaminopimelate decarboxylase (LysA) polypeptide.

SEQ ID NO: 3 is a synthetic nucleic acid primer sequence.

SEQ ID NO: 4 is a synthetic nucleic acid primer sequence.

SEQ ID NO: 5 is a synthetic nucleic acid primer sequence.

SEQ ID NO: 6 is a synthetic nucleic acid primer sequence.

SEQ ID NO: 7 is a synthetic nucleic acid primer sequence.

SEQ ID NO: 8 is a synthetic nucleic acid primer sequence.

SEQ ID NO: 9 is a synthetic nucleic acid primer sequence.

SEQ ID NO: 10 is a synthetic nucleic acid primer sequence.

SEQ ID NO: 11 is a synthetic nucleic acid primer sequence.

SEQ ID NO: 12 is a synthetic nucleic acid primer sequence.

SEQ ID NO: 13 is a synthetic nucleic acid primer sequence.

SEQ ID NO: 14 is a synthetic nucleic acid primer sequence.

SEQ ID NO: 15 is a synthetic nucleic acid primer sequence.

SEQ ID NO:16 is a synthetic nucleic acid primer sequence.

SEQ ID NO: 17 is a synthetic nucleic acid primer sequence.

SEQ ID NO: 18 is a synthetic nucleic acid primer sequence.

SEQ ID NO: 19 is a synthetic nucleic acid primer sequence.

SEQ ID NO: 20 is a synthetic nucleic acid primer sequence.

SEQ ID NO: 21 is a synthetic nucleic acid primer sequence.

SEQ ID NO: 22 is a synthetic nucleic acid primer sequence.

SEQ ID NO: 23 is a synthetic nucleic acid primer sequence.

SEQ ID NO: 24 is a synthetic nucleic acid primer sequence.

SEQ ID NO: 25 is a synthetic nucleic acid primer sequence.

SEQ ID NO: 26 is a synthetic nucleic acid primer sequence.

SEQ ID NO: 27 is a nucleic acid sequence encoding a *B. licheniformis* D-3-phosphoglycerate dehydrogenase (SerA) polypeptide of SEQ ID NO: 28.

SEQ ID NO: 28 is the amino acid sequence of a *B. licheniformis* D-3-phosphoglycerate dehydrogenase (SerA) polypeptide.

SEQ ID NO: 29 is a synthetic nucleic acid primer sequence.

SEQ ID NO: 30 is a synthetic nucleic acid primer sequence.

SEQ ID NO: 31 is a synthetic nucleic acid primer sequence.

SEQ ID NO: 32 is a synthetic nucleic acid primer sequence.

SEQ ID NO: 33 is a synthetic nucleic acid primer sequence.

SEQ ID NO: 34 is a synthetic nucleic acid primer sequence.

SEQ ID NO: 35 is a synthetic nucleic acid primer sequence.

SEQ ID NO: 36 is a synthetic nucleic acid primer sequence.

SEQ ID NO: 37 is a synthetic nucleic acid primer sequence.

SEQ ID NO: 38 is a synthetic nucleic acid primer sequence.

SEQ ID NO: 39 is a synthetic nucleic acid primer sequence.

SEQ ID NO: 40 is a synthetic nucleic acid primer sequence.

SEQ ID NO: 41 is a synthetic nucleic acid primer sequence.

SEQ ID NO: 42 is a synthetic nucleic acid primer sequence.

SEQ ID NO: 43 is a synthetic nucleic acid primer sequence.

SEQ ID NO: 44 is a synthetic nucleic acid primer sequence.

SEQ ID NO: 45 is a synthetic nucleic acid primer sequence.

SEQ ID NO: 46 is a synthetic nucleic acid primer sequence.

SEQ ID NO: 47 is a synthetic nucleic acid primer sequence.

SEQ ID NO: 48 is a synthetic nucleic acid primer sequence.

SEQ ID NO: 49 is a synthetic nucleic acid primer sequence.

SEQ ID NO: 50 is a synthetic nucleic acid primer sequence.

SEQ ID NO: 51 is a synthetic nucleic acid primer sequence.

SEQ ID NO: 52 is a synthetic nucleic acid primer sequence.

SEQ ID NO: 53 is a synthetic nucleic acid primer sequence.

SEQ ID NO: 54 is a synthetic nucleic acid primer sequence.

SEQ ID NO: 55 is a synthetic nucleic acid primer sequence.

SEQ ID NO: 56 is a synthetic nucleic acid primer sequence.

SEQ ID NO: 57 is a synthetic nucleic acid primer sequence.

SEQ ID NO: 58 is a synthetic nucleic acid primer sequence.

SEQ ID NO: 59 is a synthetic nucleic acid primer sequence.

SEQ ID NO: 60 is a synthetic nucleic acid primer sequence.

SEQ ID NO: 61 is a synthetic nucleic acid primer sequence.

SEQ ID NO: 62 is a synthetic nucleic acid primer sequence.

SEQ ID NO: 63 is a synthetic nucleic acid primer sequence.

SEQ ID NO: 64 is a synthetic nucleic acid primer sequence.

SEQ ID NO: 65 is a nucleic acid sequence encoding a *B. licheniformis* orotidine 5'-phosphate decarboxylase (PyrF) polypeptide of SEQ ID NO:66.

SEQ ID NO: 66 is the amino acid sequence of a *B. licheniformis* orotidine 5'-phosphate decarboxylase (PyrF) polypeptide.

SEQ ID NO: 67 is a nucleic acid sequence encoding a ComK protein of SEQ ID NO: 68.

SEQ ID NO: 68 is the amino acid sequence of a ComK protein.

SEQ ID NO: 69 is a synthetic nucleic acid sequence comprising a tetracycline gene.

SEQ ID NO: 70 is a synthetic nucleic acid primer sequence.

SEQ ID NO: 71 is a synthetic nucleic acid primer sequence.

DETAILED DESCRIPTION

The instant disclosure is generally related to compositions and methods for producing and constructing *Bacillus licheniformis* host cells (e.g., protein production host cells, cell factories) having increased protein production capabilities. More particularly, the present disclosure is directed to efficient genetic modifications of *Bacillus licheniformis* cells and the subsequent selection of such *Bacillus licheniformis* cells having increased protein production capabilities. Thus, certain embodiments of the disclosure are generally related to methods and compositions for producing/obtaining auxotrophic *B. licheniformis* cells, wherein certain other embodiments of the disclosure are directed to methods and compositions for restoring prototrophy in auxotrophic *B. licheniformis* cells.

For example, in particular embodiments, the disclosure is related to lysine auxotrophic *B. licheniformis* cells comprising an inactivated genomic diaminopimelate decarboxylase (lysA) gene, serine auxotrophic *B. licheniformis* cells comprising an inactivated genomic D-3-phosphoglycerate dehydrogenase (serA) gene, uracil auxotrophic *B. licheniformis* cells comprising an inactivated genomic orotidine 5'-phosphate decarboxylase (pyrF) gene and combinations thereof. Certain other embodiments are directed to compositions and methods for concurrently introducing a recombinant DNA construct into an auxotrophic *B. licheniformis* host cell (e.g., a *B. licheniformis* lysine auxotrophic cell, a *B. licheniformis* serine auxotrophic cell, a *B. licheniformis* uracil auxotrophic cell and combinations thereof) and restoring prototrophy in the *B. licheniformis* auxotrophic host cell, wherein the DNA construct comprises at least a nucleic acid sequence encoding a selectable marker (e.g., a LysA polypeptide, a SerA polypeptide, a PyrF polypeptide and combinations thereof) operably linked to a nucleic acid sequence encoding a polypeptide of interest (e.g., an amylase, a protease and the like).

For example, in certain embodiments of the disclosure, lysine auxotrophic *B. licheniformis* cells comprising an inactivated genomic lysA gene are modified by introducing a DNA construct comprising a selectable marker encoding a LysA protein, cultivating the modified cells in a growth-medium which does not comprise lysine and selecting for a host cell comprising the DNA construct that is capable of growing in the medium which does not comprise lysine. In related embodiments, the DNA construct comprising (i.e., encoding) a selectable marker protein is operably linked to a nucleic acid sequence encoding a protein of interest. In particular embodiments, the DNA construct comprises an upstream (5') nucleic acid sequence homology region (5'-HR) and a downstream (3') nucleic acid sequence homology region (3'-HR), wherein the 5'-HR and 3'-HR are sufficiently homologous with a genomic region (locus) of the host cell to effect integration into the genome by homologous recombination.

I. Definitions

In view of the auxotrophic *B. licheniformis* cells of the disclosure, the restored prototrophy *B. licheniformis* cells of the disclosure, and the compositions and methods thereof as described herein, the following terms and phrases are defined.

Unless otherwise indicated herein, one or more *Bacillus* strains (i.e., host cells) described herein can be made and used via conventional techniques commonly used in molecular biology, microbiology, protein purification, protein and DNA sequencing and various recombinant DNA methods/techniques.

Unless defined otherwise herein, all technical and scientific terms used herein have the same meaning as commonly understood by one of ordinary skill in the art.

Any definitions provided herein are to be interpreted in the context of the specification as a whole. As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. Each numerical range used herein includes every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, "the genus *Bacillus*" includes all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. gibsonii,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearother-*

*mophilus*", or *B. polymyxa*, which is now "*Paenibacillus polymyxa*". The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

As used herein, a *B. licheniformis* "chromosomal lysA gene" comprises a nucleotide sequence encoding a "diaminopimelate decarboxylase" protein (hereinafter, "LysA" protein) of SEQ ID NO: 2, a *B. licheniformis* "chromosomal serA gene" comprises a nucleotide sequence encoding a "D-3-phosphoglycerate dehydrogenase" protein (hereinafter, "SerA" protein) of SEQ ID NO: 28 and a *B. licheniformis* "chromosomal pyrF gene" comprises a nucleotide sequence encoding an "orotidine 5'-phosphate decarboxylase" (hereinafter, "PyrF" protein) of SEQ ID NO: 66.

As used herein, a "prototrophic" *Bacillus* strain, a "prototrophic" *B. licheniformis* cell, a "*Bacillus* prototroph", a "*B. licheniformis* prototroph" and the like, refer to a *B. licheniformis* cell characterized by its ability to synthesize all of the requisite organic compounds needed for growth.

In contrast, as used herein, an "auxotrophic" *Bacillus* strain, an "auxotrophic" *B. licheniformis* cell, a "*Bacillus* auxotroph", a "*B. licheniformis* auxotroph" and the like, refer to a *B. licheniformis* cell characterized by its inability to synthesize a particular organic compound required for its growth. For example, a *B. licheniformis* cell of the disclosure comprising an inactivated genomic lysA gene does not produce an active diaminopimelate decarboxylase (LysA) protein, and is therefore a lysine auxotroph; a *B. licheniformis* cell of the disclosure comprising an inactivated genomic serA gene does not produce an active D-3-phosphoglycerate dehydrogenase (serA) protein, and is therefore a serine auxotroph and a *B. licheniformis* cell of the disclosure comprising an inactivated genomicpyrF gene does not produce an active orotidine 5'-phosphate decarboxylase (PyrF) protein, and is therefore an uracil auxotroph.

Stated another way, a modified *B. licheniformis* cell of the disclosure comprising an inactivated genomic lysA gene requires a culture/growth medium supplemented with lysine for growth/survival, a modified *B. licheniformis* cell of the disclosure comprising an inactivated genomic serA gene requires a culture/growth medium supplemented with serine for growth/survival and a modified *B. licheniformis* cell of the disclosure comprising an inactivated genomic pyrF gene requires a culture/growth medium supplemented with uracil for growth/survival.

In certain embodiments, an auxotrophic *B. licheniformis* cell of the disclosure comprises at least two inactivated chromosomal genes selected from a lysA gene, a serA gene and a pyrF gene. In certain other embodiments, a *B. licheniformis* cell of the disclosure comprises an inactivated chromosomal lysA gene, an inactivated chromosomal serA gene and an inactivated chromosomal pyrF gene, wherein the *B. licheniformis* cell is a lysine, serine and uracil auxotroph.

As used herein, the phrase "restoring prototrophy" in a *Bacillus licheniformis* cell or "restored prototrophy" in a *Bacillus licheniformis* cell specifically refers to a prototrophic *B. licheniformis* (daughter) cell derived from an auxotrophic *B. licheniformis* (parental) cell. For example, a lysine auxotrophic *B. licheniformis* cell of the disclosure comprises an inactivated chromosomal lysA gene and is unable to grow in the absence of exogenously supplied lysine in the culture/growth medium. In contrast, introduction (e.g., transformation) of a DNA construct (e.g., a vector) encoding an active LysA protein into the auxotrophic *B. licheniformis* cell, subsequently results in a *B. licheniformis* (daughter) cell capable of growing without exogenously supplied lysine in the culture/growth medium, thereby having a "restored prototrophy".

As used herein, a *B. licheniformis* "chromosomal lysA gene" comprises a nucleotide sequence of SEQ ID NO: 1 (or a degenerate sequence thereof) encoding a LysA protein of SEQ ID NO: 2. In certain embodiments, a *B. licheniformis* chromosomal lysA gene comprises a nucleotide sequence encoding a LysA protein comprising at least 90% sequence identity to the LysA protein of SEQ ID NO: 2, wherein a LysA protein having at least 90% sequence identity to SEQ ID NO: 2 comprises diaminopimelate decarboxylase activity. In certain other embodiments, a *B. licheniformis* chromosomal lysA gene encodes a LysA protein having at least 80% sequence identity to SEQ ID NO: 2, with the proviso that such *B. licheniformis* host cells comprising a chromosomal lysA gene encoding a LysA protein having at least 80% sequence identity to SEQ ID NO: 2 comprise sufficient diaminopimelate decarboxylase activity that the *B. licheniformis* host cells are capable of growing in a growth medium which does not comprise lysine.

As used herein, a *B. licheniformis* "chromosomal serA gene" comprises a nucleotide sequence of SEQ ID NO: 27 (or a degenerate sequence thereof) encoding a SerA protein of SEQ ID NO: 28. In certain embodiments, a *B. licheniformis* chromosomal serA gene comprises a nucleotide sequence encoding a SerA protein comprising at least 90% sequence identity to the SerA protein of SEQ ID NO: 28, wherein a SerA protein having at least 90% sequence identity to SEQ ID NO: 28 comprises D-3-phosphoglycerate dehydrogenase activity. In certain other embodiments, a *B. licheniformis* chromosomal serA gene encodes a SerA protein having at least 80% sequence identity to SEQ ID NO: 28, with the proviso that such *B. licheniformis* host cells comprising a chromosomal serA gene encoding a SerA protein having at least 80% sequence identity to SEQ ID NO: 28 comprise sufficient D-3-phosphoglycerate dehydrogenase activity that the *B. licheniformis* host cells are capable of growing in a growth medium which does not comprise serine.

As used herein, a *B. licheniformis* "chromosomal pyrF gene" comprises a nucleotide sequence of SEQ ID NO: 67 (or a degenerate sequence thereof) encoding a PyrF protein of SEQ ID NO: 66. In certain embodiments, a *B. licheniformis* chromosomal pyrF gene comprises a nucleotide sequence encoding a PyrF protein comprising at least 90% sequence identity to the PyrF protein of SEQ ID NO: 66, wherein a PyrF protein having at least 90% sequence identity to SEQ ID NO: 66 comprises orotidine 5'-phosphate decarboxylase activity. In certain other embodiments, a *B. licheniformis* chromosomal pyrF gene encodes a PyrF protein having at least 80% sequence identity to SEQ ID NO: 66, with the proviso that such *B. licheniformis* host cells comprising a chromosomal pyrF gene encoding a PyrF protein having at least 80% sequence identity to SEQ ID NO: 66 comprise sufficient orotidine 5'-phosphate decarboxylase activity that the *B. licheniformis* host cells are capable of growing in a growth medium which does not comprise uracil.

As used herein, a "genetically modified cell", a "genetically modified host cell", a "genetically modified *B. licheniformis* cell", a "modified cell" and the like are used interchangeably, and refer to a recombinant *B. licheniformis* cell that comprises at least one genetic modification which is not present in a "parental" *B. licheniformis* cell from which the modified *B. licheniformis* (daughter) cell is derived.

As used herein, the terms "modification", "genetic modification", "genetic alteration" and "genetic manipulation" are used interchangeably and include, but are not limited to: (a) the introduction, substitution, or removal of one or more nucleotides in a gene (or an open reading frame (ORF) thereof), or the introduction, substitution, or removal of one or more nucleotides in a regulatory element required for the transcription or translation of the gene (or ORF thereof), (b) a gene disruption, (c) a gene conversion, (d) a gene deletion, (e) a down-regulation of a gene, (f) an up-regulation of a gene, (g) specific mutagenesis and/or (h) random mutagenesis of any one or more the nucleic acid sequence or genes disclosed herein. For example, as used herein a genetic modification includes, but is not limited to, a modification of one or more genes selected from the group consisting of a *Bacillus licheniformis* lysA gene, a *Bacillus licheniformis* serA gene, a *Bacillus licheniformis* pyrF gene, and the like.

As used herein, "disruption of a gene", "gene disruption", "inactivation of a gene" and "gene inactivation" are used interchangeably and refer broadly to any genetic modification that substantially prevents a host cell from producing a functional gene product (e.g., a protein). Exemplary methods of gene disruptions include the complete or partial deletion of any portion of a gene, including a polypeptide-coding sequence (e.g., an ORF), a promoter sequence, an enhancer sequence, or another regulatory element sequence, or mutagenesis of the same, where mutagenesis encompasses substitutions, insertions, deletions, inversions, and any combinations and variations thereof which disrupt/inactivate the target gene(s) and substantially reduce or prevent the production of the functional gene product (i.e., a protein).

As used herein, the terms "down-regulation" of gene expression and "up-regulation" of gene expression include any method that results in lower (down-regulated) or higher (up-regulated) expression of a given gene. For example, the down-regulation of a gene can be achieved by RNA-induced gene silencing, genetic modifications of control elements (e.g., such as the promoter, ribosomal binding site (RBS)/Shine-Dalgarno sequences, untranslated regions (UTRs)), codon changes, and the like.

As used herein, "host cell" refers to a cell that has the capacity to act as a host or expression vehicle for a newly introduced DNA sequence (e.g., such as a vector/DNA construct). In certain embodiments, a host cells of the disclosure is a member of the genus *Bacillus*.

As defined herein, the terms "increased expression", "enhanced expression", "increased expression of a POI", "increased production", "increased production of a POI" and the like refer to a "modified" *B. licheniformis* (daughter) cell derived from a parental *B. licheniformis* cell, wherein the "increase" is always relative (vis-à-vis) to the "unmodified" *B. licheniformis* (parental) cell expressing/producing the same POI.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As defined herein, the combined term "expresses/produces", as used in phrases such as "a modified host cell expresses/produces an increased amount of a protein of interest relative to the (unmodified) parental host cell", the term ("expresses/produces") is meant to include any steps involved in the expression and production of a protein of interest in host cell of the disclosure.

As used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "open reading frames" (ORFs), "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As defined herein, the term "LAT amylase" refers to the B. licheniformis α-amylase "AmyL", and as such, the terms may be used interchangeably.

As used herein, "a functional promoter sequence controlling the expression of a gene of interest (or open reading frame thereof) linked to the gene of interest's protein coding sequence" refers to a promoter sequence which controls the transcription and translation of the coding sequence in Bacillus. For example, in certain embodiments, the present disclosure is directed to a polynucleotide (e.g., a DNA construct) comprising a 5' promoter (or a 5' promoter region, or tandem 5' promoters and the like), wherein the promoter region is operably linked to a nucleic acid sequence encoding a selectable marker or a gene of interest (GOI) encoding a protein of interest (POI). Thus, in certain embodiments, a functional promoter sequence controls the expression of a lysA gene (or ORF thereof) and/or a serA gene (or ORF thereof) and/or a pyrF gene (or ORF thereof) and/or a GOI encoding a POI. In certain embodiments, the functional promoter sequence used is the native promoter nucleic acid sequence as associated with the wild-type (native) lysA gene, serA gene, pyrF gene or GOI as isolated in nature. In other embodiments, the functional promoter sequence used is a heterologous promoter nucleic acid sequence which is not associated with the wild-type (native) lysA gene, serA gene, pyrF gene or GOI as isolated in nature, wherein the heterologous promoter is a constative promoter or an inducible promoter.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a bacterial cell" or "introducing into a B. licheniformis cell" at least one polynucleotide open reading frame (ORF), or a gene thereof, or a vector/DNA construct thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). For example, in certain embodiments of the disclosure, a parental B. licheniformis cell is modified (e.g., transformed) by introducing into the parental cell a DNA construct which inactivates prototrophy of the B. licheniformis cell, thereby resulting in an auxotrophic B. licheniformis daughter cell. Likewise, in certain other embodiments, an auxotrophic B. licheniformis (daughter) cell is modified (e.g., transformed) by introducing into the auxotrophic B. licheniformis (daughter) cell a DNA construct which restores prototrophy of the B. licheniformis cell, wherein the introduced DNA construct further comprises a nucleic acid sequence (e.g., a gene or ORF) encoding a protein of interest (POI).

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other preferred embodiments it further comprises an incoming sequence flanked by homology regions (HR). In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein, a "homology region" (abbreviated "HR") such as a "5'-HR" or a "3'-HR" disclosed herein, refers to a nucleic acid sequence, which is homologous to a sequence in the Bacillus licheniformis chromosome. More specifically, a homology region (HR) is an upstream or downstream region having between about 80 and 100% sequence identity, between about 90 and 100% sequence identity, or between about 95 and 100% sequence identity with the immediate flanking coding region of a gene, or part of a gene to be deleted, disrupted, inactivated, down-regulated and the like, according to the instant disclosure. These HR sequences direct where in the B. licheniformis chromosome a DNA construct is integrated, and directs what part of the B. licheniformis chromosome is replaced by the incoming sequence. Thus, in certain embodiments, an incoming sequence is flanked by a homology region (HR) on each side. In other embodiments, the incoming sequence and the HR comprise a unit that is flanked by stuffer sequence on each side. In some embodiments, a homology region (HR sequence) is present on only a single side (either 3' or 5'), whereas in other embodiments, it is on each side of the sequence being flanked. The sequence of each homology region is therefore homologous to a sequence in the *Bacillus* chromosome.

As used herein, the term "stuffer sequence" refers to any extra DNA that flanks the 5'-HR and/or the 3'-HR homology regions (e.g., vector sequences).

Thus, while not meant to limit the present disclosure, a homology region (HR) may include about between 1 base pair (bp) to 200 kilobases (kb). Preferably, a homology region (HR) includes about between 1 bp and 10.0 kb; between 1 bp and 5.0 kb; between 1 bp and 2.5 kb; between 1 bp and 1.0 kb, and between 0.25 kb and 2.5 kb. A homology region may also include about 10.0 kb, 5.0 kb, 2.5 kb, 2.0 kb, 1.5 kb, 1.0 kb, 0.5 kb, 0.25 kb and 0.1 kb. For example, in some embodiments, the 5' and 3' ends of a selective marker (e.g., a lysA gene, a serA gene, a pyrF gene and the like) are flanked by a homology region (5'-HR/3'-HR) wherein the homology region comprises nucleic acid sequences immediately flanking the coding region of the gene.

As used herein, the terms "selectable marker" and "selective marker" refer to a nucleic acid (e.g., a gene or ORF) capable of expression in host cell, which allows for ease of selection of those host cells containing the selectable marker vector/DNA construct. Thus, the term "selectable marker" refers to genes (or ORFs) that provide an indication that a host cell has taken up an incoming DNA construct of interest.

As defined herein, a host cell "genome", a bacterial (host) cell "genome", or a *B. licheniformis* (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "vector" refers to any nucleic acid that can be replicated (propagated) in cells and can carry new genes (or ORFs or DNA segments) into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

As used herein, the terms "expression cassette" and "expression vector" refer to a nucleic acid (DNA) construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing or removing mutations in the chromosome of a host cell through homologous recombination. In certain embodiments, such targeting vectors are usefully employed in inactivating one or more genes in (parental) *B. licheniformis* cells to obtain auxotrophic *B. licheniformis* (daughter) cells thereof. For example, in certain embodiments, a targeting vector is used to inactivate *B. licheniformis* genes including, but not limited to, a lysA gene, a serA gene, a pyrF gene, and combinations thereof. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is well within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a modified *B. licheniformis* host cell, wherein the POI is preferably expressed at increased levels (i.e., relative to the "unmodified" (parental) cell). Thus, as used herein, a POI may be an enzyme, a substrate-binding protein, a surface-active protein, a structural protein, a receptor protein, and the like. In certain embodiments, a modified cell of the disclosure produces an increased amount of a heterologous protein of interest or an endogenous protein of interest relative to the parental cell. In particular embodiments, an increased amount of a protein of interest produced by a modified cell of the disclosure is at least a 0.5% increase, at least a 1.0% increase, at least a 5.0% increase, or a greater than 5.0% increase, relative to the parental cell.

Similarly, as defined herein, a "gene of interest" or "GOI" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., acetyl esterases, aryl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer.

As defined herein, a "heterologous" nucleic acid construct or a "heterologous" nucleic acid sequence has a portion of the sequence which is not native to the cell in which it is expressed.

The term "derived" encompasses the terms "originated", "obtained", "obtainable" and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using computer programs and techniques known in the art, (See e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.) and Devereux et. al., 1984).

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the term "ComK polypeptide" is defined as the product of a comK gene; a transcription factor that acts as the final auto-regulatory control switch prior to competence development; involved with activation of the expression of late competence genes involved in DNA-binding and uptake and in recombination (Liu and Zuber, 1998, Hamoen et al., 1998). In certain embodiments of the disclosure, a *B. licheniformis* host cell comprises an introduced plasmid (pB1ComK) encoding the comK transcription factor. Exemplary ComK nucleic acid and polypeptide sequences are set forth in SEQ ID NO: 67 and SEQ ID NO: 68, respectively.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "orthologue" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, an "analogous sequence" is one wherein the function of the gene is essentially the same as the gene derived from a *B. licheniformis* cell. Additionally, analogous genes include at least 60%, 65%, 70%, 75%, 80%, 85%, 90%, 95%, 97%, 98%, 99% or 100% sequence identity with the sequence of the *Bacillus licheniformis* cell. Analogous sequences are determined by known methods of sequence alignment. A commonly used alignment method is BLAST, although there are other methods that also find use in aligning sequences.

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$ −5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5% SDS at room temperature (RT) and two additional times in 0.1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denaturated sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination", "recombining" or generating a "recombined" nucleic acid is generally the assembly of two or more nucleic acid fragments wherein the assembly gives rise to a chimeric gene.

II. Producing Auxotrophic *B. licheniformis* Cells and Restoring Prototrophy in Such Auxotrpohic *B. licheniformis* Cells As set forth above, certain embodiments of the instant disclosure are related to compositions and methods for producing and constructing *Bacillus licheniformis* host cells (e.g., protein production host cells, cell factories) having increased protein production capabilities. More particularly, certain embodiments of the disclosure are directed to genetic modifications of *B. licheniformis* cells and the subsequent selection of such *B. licheniformis* cells having increased protein production capabilities. Thus, certain embodiments of the disclosure are generally related to methods and compositions for producing/obtaining auxotrophic *B. licheniformis* cells, wherein certain other embodiments of the disclosure are directed to methods and compositions for restoring prototrophy in auxotrophic *B. licheniformis* cells.

For example, as presented in Example 1 of the instant disclosure, a lysine auxotrophic *B. licheniformis* (daughter) cell was obtained by deleting the complete lysA gene (SEQ ID NO: 1) in a parental *B. licheniformis* cell, which deletion included 67 bp upstream (5') and 68 bp downstream (3') of the lysA gene. As presented in Example 1, the lysA gene (SEQ ID NO: 1) of the parental *B. licheniformis* cell encodes a LysA protein comprising the amino acid sequence set forth in SEQ ID NO: 2.

Thus, to engineer a lysA deletion, the upstream (5') flanking region and downstream (3') flanking region were amplified from the genomic DNA of the (parental) *B. licheniformis* cell (i.e., referred to as Host Cell 1 in Example 1). Thus, "Host Cell 1" is a prototrophic *B. licheniformis* parental cell. After gel purification of the amplicons, the purified upstream and downstream flanking amplicons were fused together. Likewise, the fused amplicon was gel purified, followed by restriction digestion, and the digested amplicon was gel purified and ligated into a "XhoI" and "NotI" digested and gel purified "pCZ105" (see, FIG. 1).

Figure 2:
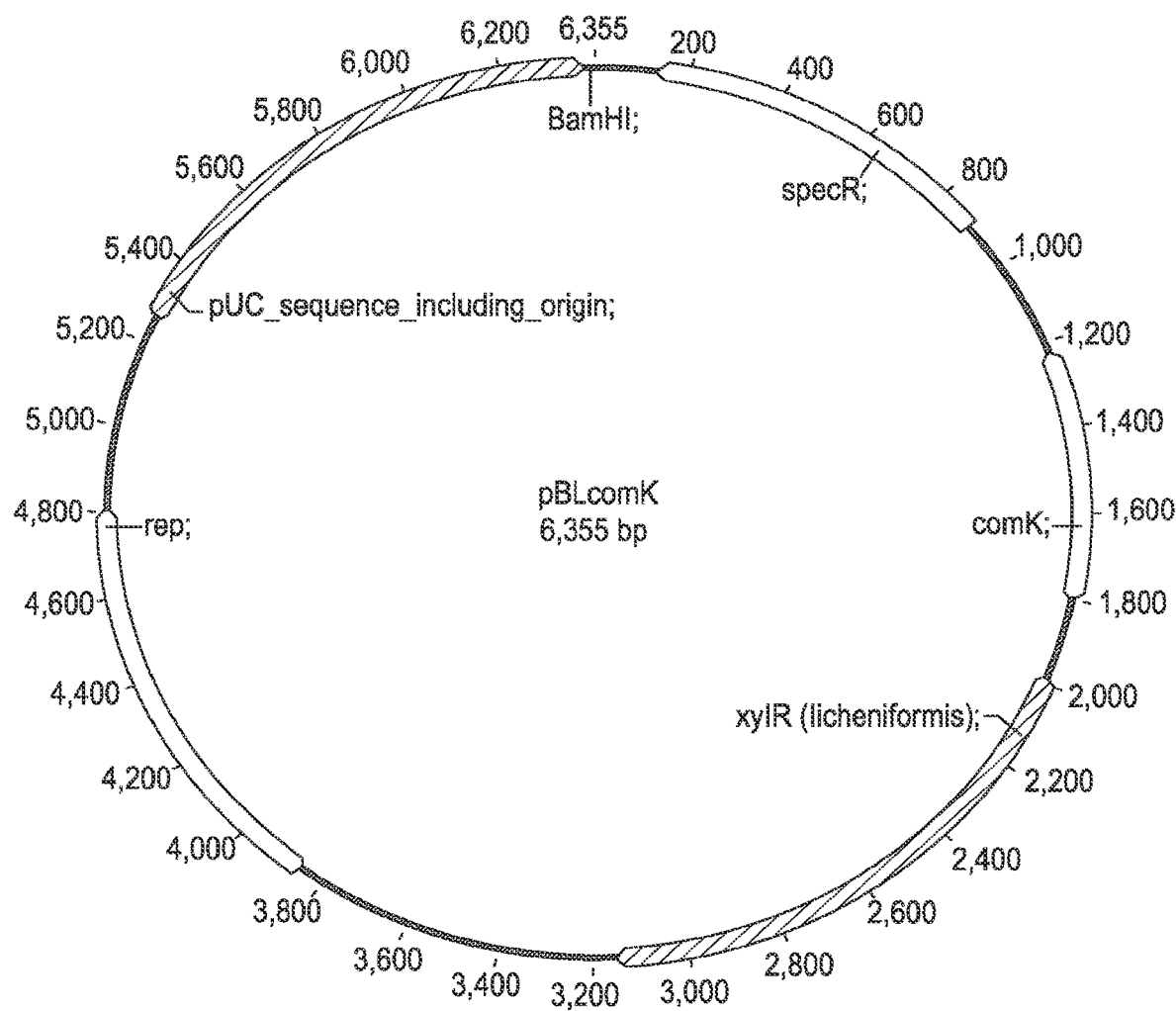
FIG. 2 shows a plasmid map of vector pBLcomK. Plasmid pBLcomK includes DNA sequences encoding the pBR322 origin of replication, the *Enterococcus faecalis* Spectinomycin resistance (Spec') gene spc (also called aad9), the *B. subtilis* (natto) plasmid pTA1060 rep gene for replication in Bacilli, the *B. licheniformis* comK gene controlled by the *B. subtilis* xylA promoter, and the *B. subtilis* xylR gene.

The rolling circle amplified ("RCA") mix of the pCZ105 plasmid harboring the fused up and downstream region of the lysA locus was transformed into competent (parental) *B. licheniformis* cells comprising (harboring) a pBLcomK plasmid (i.e., Host Cell 2 in Example 1; see, FIG. 2) as generally described in International PCT Publication Nos. WO2017/075195, WO2002/14490 and WO2008/7989. Thus, "Host Cell 2" is a prototrophic *B. licheniformis* (daughter) cell derived from Host Cell 1, wherein Host Cell 2 comprises the introduced plasmid pBLcomK (e.g., see Table 1 in Examples Section).

Subsequently, formed colonies were inoculated in Luria broth (containing 30 mg/l kanamycin) and incubated overnight at 42° C. to promote single crossover integration in the genome, followed by plating on Luria agar containing 30 mg/l kanamycin. Double crossover integration was obtained by culturing the correct single crossover integrants in Luria broth overnight at 37° C., followed by plating onto Luria agar. Colonies unable to grow in the presence of 30 mg/L Kanamycin were tested by PCR for double crossover integration.

For verification of a lysine auxotrophy in the modified *B. licheniformis* (daughter) cells (i.e., daughter cells of Host Cell 2), four (4) colonies of this modified strain (referred to a Host Cell 3 (ΔlysA) in Example 1), as well as *B. licheniformis* Host Cell 2, were cultured in 20 mL Luria broth over night at 37° C. while shaking. For example, as presented in FIG. 3 of the instant disclosure, the Host Cell 3 (ΔlysA) colonies showed no growth without addition of D-lysine, in contrast to the prototrophic (parental) Host Cell 2. Furthermore, the addition of 10-50 μg/ml D-lysine enabled growth of the Host Cell 3 (ΔlysA) colonies, demonstrating that the engineered (daughter) Host Cell 3 is lysine auxotrophic. Likewise, Example 7 and Example 9 of the instant disclosure describe compositions and methods for obtaining serine (ΔserA) auxotrophic *B. licheniformis* cells and uracil (ΔpyrF) auxotrophic *B. licheniformis* cells, respectively. Thus, in certain embodiments, modified *B. licheniformis* cells of the disclosure comprise at least one auxotrophic phenotype selected from lysine auxotrophy, serine auxotrophy and uracil auxotrophy, or at least two auxotrophic phenotypes selected from lysine auxotrophy, serine auxotrophy and uracil auxotrophy. In other embodiments, modified *B. licheniformis* cells of the disclosure are auxotrophic for lysine, serine and uracil.

Figure 4:
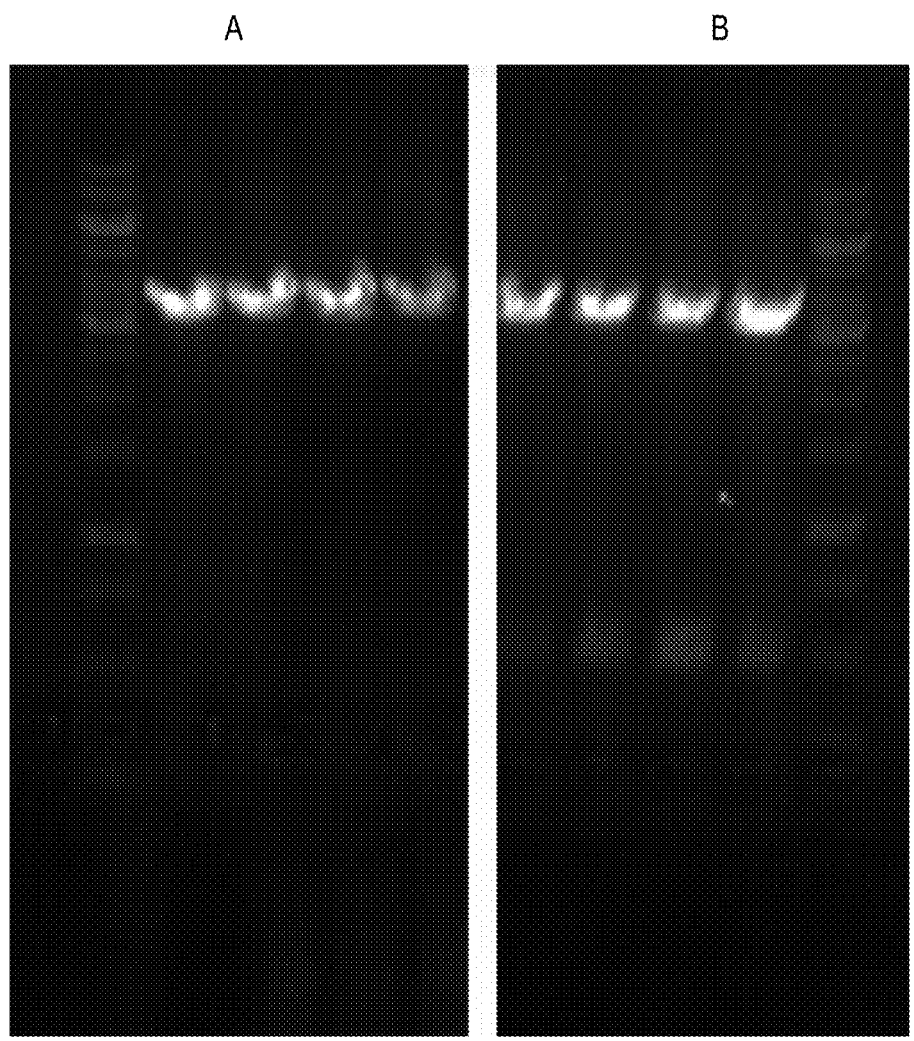
FIG. 4 shows an agarose gel of the amplicons of the lysA locus using forward primer 5 and reverse primer 5 (upstream) [FIG. 4, panel A] and forward primer 6 and reverse primer 6 (downstream) [FIG. 4, panel B]. The marker used here is the GeneRuler 1 kb DNA Ladder (Thermoscientific, Breda, the Netherlands).

Example 2 of the instant disclosure describes methods and compositions for restoring prototrophy in the lysine auxotrophic *B. licheniformis* cells (Host Cell 3 "ΔlysA") described in Example 1. More specifically, to evaluate whether prototrophy of *B. licheniformis* Host Cell 3 (ΔlysA) can be restored by re-introducing the lysA gene into the genome, *B. licheniformis* Host Cell 3 (ΔlysA) was transformed with the intact lysA gene and 1.3 kb HR flanks (on either side of the lysA ORF). Thus, the *B. licheniformis* Host Cell 3 (ΔlysA) cells (comprising pBLComK) were made competent as described previously, wherein 3 ag of amplified linear product was added to Host Cell 3 (ΔlysA) to promote double crossover integration of the amplicon in the genome, thereby eliminating lysine auxotrophy and restoring prototrophy in *B. licheniformis* (daughter) cells derived therefrom. Thus, the Host Cell 4 (restored) is a "restored prototrophy" *B. licheniformis* (daughter) cell derived from *B. licheniformis* Host Cell 3 (ΔlysA). For example, no colonies were observed on minimal M9 agar plates on the control (H₂O) transformation, indicating this strain remained lysine (LysA) auxotrophic. In contrast, Host Cell 4 (restored), yielded colonies, thereby indicating this strain was prototrophic, wherein the lysA locus was restored. More particularly, as shown in FIG. 4A and FIG. 4B, both PCR amplifications yielded product (3.3 KB), indicating the lysA gene was correctly integrated in the correct locus, restoring the lysA gene in its original (chromosomal) locus.

Furthermore, Example 3 of the instant disclosure demonstrates the use of the lysA gene as a selectable marker for expressing a gene of interest in a lysine auxotrophic *B. licheniformis* (e.g., ΔlysA) background. For example, a linear construct was engineered, harboring on the 5' end a homology region (5'-HR) to the lysA locus and the intact lysA gene, an α-amylase coding sequence flanked by a promoter and terminator region, and a 3' homology region (3'-HR) to the lysA locus. The results presented in Example 3 confirm that the (lysine) auxotrophic *B. licheniformis* cells transformed with the "selectable marker-amylase" construct set forth above (e.g., 5' HR-lysA-amylase-3' HR or 5' HR-amylase-lysA-3' HR), have restored prototrophy, as indicated by their ability to grow in the absence of exogenously supplied lysine. Likewise, the activity of the introduced α-amylase coding sequence was confirmed using a Ceralpha α-amylase assay, clearly indicating the functional expression of a gene of interest (GOI) in the lysA locus using lysA as a selectable marker.

In addition, Example 4 of the instant disclosure demonstrates the use of the lysA gene as a selectable marker for expressing a gene of interest in a lysine auxotrophic *B. licheniformis* (e.g., ΔlysA) background, wherein the "selectable marker-amylase" construct set forth above is integrated/targeted into a *B. licheniformis* locus outside of the lysA locus. More specifically, the results set forth in Example 4 of the instant disclosure confirm that (lysine) auxotrophic *B. licheniformis* cells transformed with the "selectable marker-amylase" construct set forth above (e.g., 5' HR-lysA-amylase-3' HR or 5' HR-amylase-lysA-3' HR), which construct was introduced into different loci of the *B. licheniformis* genome, have restored prototrophy, as indicated by their ability to grow in the absence of exogenously supplied lysine. Likewise, the activity of the introduced α-amylase coding sequence was confirmed using a Ceralpha α-amylase assay, clearly indicating the functional expression of a gene of interest (GOI) in a *B. licheniformis* genomic locus outside of the lysA locus. Moreover, four (4) additional loci (e.g., amyL locus, katE locus, pdp locus and catH locus) were used for integration a gene of interest (GOI) using the lysA gene as a selectable marker, all yielding the same results as described above and indicating the functional expression of the GOI when using the lysA gene as a selectable marker outside of its original (lysA) locus.

Example 5 of the instant disclosure further demonstrates that partial deletions of the *B. licheniformis* (chromosomal) lysA gene also renders such *B. licheniformis* (daughter) cells auxotrophic for lysine, as colonies only appeared in growth medium supplemented with lysine. Additionally, Example 6 of the disclosure demonstrates that single point mutations (i.e., 1-bp deletions) in the *B. licheniformis* lysA gene sequence also render such *B. licheniformis* cells auxotrophic for lysine, as colonies only appeared in growth medium supplemented with lysine.

Likewise, Example 8 of the instant disclosure demonstrates the use of the serA gene as a selectable marker for expressing a gene of interest in a serine auxotrophic *B. licheniformis* (e.g., ΔserA) background. More particularly, a serine auxotrophic *B. licheniformis* host cell (ΔserA, described in Example 7) was used to express an α-amylase of interest, wherein a linear construct was engineered harboring on the 5' flank (HR) the serA locus, an α-amylase sequence flanked by a 5' a promoter and 3' terminator region, and a 3' HR (which included the intact serA gene and promoter region). After picking and patching formed halo forming colonies onto fresh M9 minimal agar medium plates, the activity of the introduced α-amylase variant was confirmed using a Ceralpha α-amylase assay, clearly indicating the functional expression of an α-amylase (GOI) in the serA locus using serA as a selectable marker.

Example 10 of the disclosure further demonstrates the efficient and reliable use of multiple selectable markers for expressing multiple copies of a single gene of interest and/or the use multiple selectable markers for expressing different genes of interest in an auxotrophic *B. licheniformis* background. For example, a *B. licheniformis* host cell comprising a deleted lysA (ΔlysA) locus and a deleted serA (ΔserA) locus was used to express two (2) copies of an α-amylase gene. As set forth in Example 10, clones were obtained with the correct integration of both copies of the α-amylase using lysA locus and serA locus, thereby restoring prototrophy in these cells and demonstrating the functional expression of two copies of the active α-amylase gene product. Furthermore, Example 11 describes the use of the lysA gene, the serA gene and/or the pyrF gene as selectable markers for expressing a protease (POI) in one or more *B. licheniformis* auxotrophic cells of the disclosure.

In addition, Example 12 describes the surprising and unexpected result that auxotrophic *B. licheniformis* cells of the disclosure comprise increased transformation efficiency when transformed with a linear DNA fragment comprising a selectable marker of the disclosure (e.g., lysA, serA, pyrF). For example, as presented in Example 12, such auxotrophic *B. licheniformis* cells, when transformed with a linear DNA fragment comprising a selectable marker of the disclosure, comprise a significant improvement in transformation efficiency (e.g., a 100-fold increase in CFU count) relative to (parental) *B. licheniformis* cells transformed with a linear DNA fragment comprising, for example, a chloramphenicol antibiotic marker.

Thus, in particular embodiments, the disclosure is related to lysine auxotrophic *B. licheniformis* cells comprising an inactivated genomic diaminopimelate decarboxylase (lysA) gene, serine auxotrophic *B. licheniformis* cells comprising an inactivated genomic D-3-phosphoglycerate dehydrogenase (serA) gene, uracil auxotrophic *B. licheniformis* cells comprising an inactivated genomic orotidine 5'-phosphate decarboxylase (pyrF) gene and combinations thereof. Thus, certain other embodiments are directed to compositions and methods for concurrently introducing a recombinant DNA construct into an auxotrophic *B. licheniformis* host cell (e.g., a *B. licheniformis* lysine auxotrophic cell, a *B. licheniformis* serine auxotrophic cell, a *B. licheniformis* uracil auxotrophic cell and combinations thereof) and restoring prototrophy in the *B. licheniformis* auxotrophic host cell, wherein the DNA construct comprises at least a nucleic acid sequence encoding a selectable marker (e.g., a LysA polypeptide, a SerA polypeptide, a PyrF polypeptide and combinations thereof). In other embodiments, more than one DNA construct is used, wherein a first DNA construct encodes a lysA gene, a second DNA construct encodes a serA gene, a third DNA construct encodes a pyrF gene, etc. In certain preferred embodiments, the first, second, third, etc. DNA construct comprises an operably linked nucleic acid sequence encoding a polypeptide of interest (e.g., an amylase, a protease and the like), wherein the encoded POI can be the same protein or different proteins.

III. Molecular Biology

As set forth above, certain embodiments of the disclosure are related to (recombinant) genetically modified *B. licheniformis* cells derived from parental *B. licheniformis* cells. In particular embodiments, a parental *B. licheniformis* cell is genetically modified to inactivate one or more (endogenous) chromosomal genes. In particular embodiments, a parental *B. licheniformis* cell is genetically modified to inactivate one or more (endogenous) chromosomal genes selected from a lysA gene, a serA gene and apyrF gene. In other embodiments, an auxotrophic *B. licheniformis* cell of the disclosure is genetically modified to restore prototrophy thereof. In yet other embodiments, a *B. licheniformis* cell of the disclosure is genetically modified for increased expression/production of one or more proteins of interest.

Thus, certain embodiments of the disclosure are generally related to compositions and methods for producing and constructing *B. licheniformis* host cells (e.g., protein production host cells, cell factories) having increased protein production capabilities. In other embodiments, the disclosure is directed to efficient genetic modifications of *B. licheniformis* cells and the subsequent selection of such *B. licheniformis* cells having increased protein production capabilities. Thus, in particular embodiments the disclosure is related to methods for genetically modifying *B. licheniformis* cells, wherein the modification comprises (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) a gene down-regulation, (f) site specific mutagenesis and/or (g) random mutagenesis. For example, as used herein a genetic modification includes, but is not limited to, a modification of one or more genes selected from the group consisting of a *B. licheniformis* lysA gene, serA gene, pyrF gene, and combinations thereof.

Thus, in certain embodiments, a modified *Bacillus* cell of the disclosure is constructed by reducing or eliminating the expression of a gene set forth above, using methods well known in the art, for example, insertions, disruptions, replacements, or deletions. The portion of the gene to be modified or inactivated may be, for example, the coding region or a regulatory element required for expression of the coding region. An example of such a regulatory or control sequence may be a promoter sequence or a functional part thereof, (i.e., a part which is sufficient for affecting expression of the nucleic acid sequence). Other control sequences for modification include, but are not limited to, a leader sequence, a pro-peptide sequence, a signal sequence, a transcription terminator, a transcriptional activator and the like.

In certain other embodiments, a modified *B. licheniformis* cell is constructed by gene deletion to eliminate or reduce the expression of at least one of the aforementioned genes of the disclosure. Gene deletion techniques enable the partial or complete removal of the gene(s), thereby eliminating their expression, or expressing a non-functional (or reduced activity) protein product. In such methods, the deletion of the gene(s) may be accomplished by homologous recombination, e.g., using a plasmid/vector that has been constructed to contiguously contain the 5' and 3' regions flanking (i.e., 5'HR and 3'HR) the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art (e.g., by reference to the lysA, serA, pyrF gene (nucleic acid) sequences and the encoded protein sequences thereof), may readily identify nucleotide regions in the gene's coding sequence and/or the gene's non-coding sequence suitable for complete or partial deletion.

In other embodiments, a modified *B. licheniformis* cell of the disclosure is constructed by introducing, substituting, or removing one or more nucleotides in the gene or a regulatory element required for the transcription or translation thereof.

For example, nucleotides may be inserted or removed so as to result in the introduction of a stop codon, the removal of the start codon, or a frame-shift of the open reading frame. Such a modification may be accomplished by site-directed mutagenesis, or PCR generated mutagenesis, in accordance with methods known in the art (e.g., see, Botstein and Shortie, 1985; Lo et al., 1985; Higuchi et al., 1988; Shimada, 1996; Ho et al., 1989; Horton et al., 1989 and Sarkar and Sommer, 1990). Thus, in certain embodiments, a gene of the disclosure is inactivated by complete or partial deletion.

In another embodiment, a modified *B. licheniformis* cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *B. licheniformis* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *B. licheniformis* cell is constructed by established anti-sense techniques using a nucleotide sequence complementary to the nucleic acid sequence of the gene (Parish and Stoker, 1997). More specifically, expression of a lsyA gene, a serA gene and/or a pyrF gene by a *B. licheniformis* cell can be reduced (down-regulated) or eliminated by introducing a nucleotide sequence complementary to the nucleic acid sequence of the gene, which may be transcribed in the cell and is capable of hybridizing to the mRNA produced in the cell. Under conditions, allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *B. licheniformis* cell is produced/constructed via CRISPR-Cas9 editing. For example, a gene encoding a LysA protein, SerA protein, a PyrF protein and the like, can be disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify edited colonies.

In yet other embodiments, a modified *B. licheniformis* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

In certain other embodiments, a modified *B. licheniformis* cell comprises a deletion of an endogenous (chromosomal) gene selected from lysA, serA and pyrF.

In other embodiments, a modified *B. licheniformis* cell comprises a disruption of an endogenous (chromosomal) gene selected from lysA, serA and pyrF.

In other embodiments, a modified *B. licheniformis* cell comprises a down-regulated endogenous (chromosomal) gene selected from lysA, serA and pyrF. For example, in certain embodiments, down-regulating one or more genes set forth above comprises deleting or disrupting the gene's upstream or downstream regulatory elements.

PCT Publication No. WO2003/083125 discloses methods for modifying *Bacillus* cells, such as the creation of *Bacillus* deletion strains and DNA constructs using PCR fusion to bypass *E. coli*.

PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus* spp.) (e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, *B. licheniformis* host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure of the disclosure are generally chosen so that they are functional in the *Bacillus* cells (e.g., *B. licheniformis* cells). Promoters useful for driving gene expression in *Bacillus* cells include, but are not limited to, the *B. subtilis* alkaline protease (aprE) promoter (Stahl et al., 1984), the α-amylase promoter of *B. subtilis* (Yang et al., 1983), the α-amylase promoter of *B. amyloliquefaciens* (Tarkinen et al., 1983), the neutral protease (nprE) promoter from *B. subtilis* (Yang et al., 1984), a mutant aprE promoter (PCT Publication No. WO2001/51643) or any other promoter from *B licheniformis* or other related Bacilli. Methods for screening and creating promoter libraries with a range of activities (promoter strength) in *Bacillus* cells is described in PCT Publication No. WO2003/089604.

IV. Culturing *B. licheniformis* Cells for Production of a Protein of Interest

In certain embodiments the disclosure provides methods and compositions for increasing the protein productivity of a modified *B. licheniformis* cell, as compared (i.e., relative, vis-à-vis) to an unmodified (parental) cell. Thus, in certain embodiments the disclosure provides methods of producing a protein of interest (POI) comprising fermenting/cultivating a modified *B. licheniformis* cell, wherein the modified cell secrets the POI into the culture medium. Fermentation methods well known in the art can be applied to ferment the modified and unmodified *B. licheniformis* cells of the disclosure.

For example, in some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

V. Proteins of Interest Produced by Modified (Host) Cells

A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

Thus, in certain embodiments, a modified cell of the disclosure expresses an endogenous POI, a heterologous POI or a combination of one or more thereof.

In certain embodiments, a modified *Bacillus* cell of the disclosure exhibits an increased specific productivity (Qp) of a POI relative the (unmodified) parental *Bacillus* cell. For example, the detection of specific productivity (Qp) is a suitable method for evaluating protein production. The specific productivity (Qp) can be determined using the following equation:

$$\text{``}Qp=gP/\text{gDCW}\cdot\text{hr''}$$

wherein, "gP" is grams of protein produced in the tank; "gDCW" is grams of dry cell weight (DCW) in the tank and "hr" is fermentation time in hours from the time of inoculation, which includes the time of production as well as growth time.

Thus, in certain other embodiments, a modified *Bacillus* cell of the disclosure comprises a specific productivity (Qp) increase of at least about 1%, at least about 5%, at least about 6%, at least about 7%, at least about 8%, at least about 9%, or at least about 10% or more as compared to the unmodified (parental) cell.

In certain embodiments, a POI or a variant POI thereof is selected from the group consisting of acetyl esterases, aryl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

For example, in certain embodiments a POI is an oxidoreductase enzyme, including, but not limited to, an EC 1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase) EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease S1), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-β-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.-(e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase)9

Thus, in certain embodiments, industrial protease producing *Bacillus* host cells provide particularly preferred expression hosts. Likewise, in certain other embodiments, industrial amylase producing *Bacillus* host cells provide particularly preferred expression hosts.

For example, there are two general types of proteases which are typically secreted by *Bacillus* spp., namely neutral (or "metalloproteases") and alkaline (or "serine") proteases. For example, *Bacillus* subtilisin proteins (enzymes) are exemplary serine proteases for use in the present disclosure. A wide variety of *Bacillus* subtilisins have been identified and sequenced, for example, subtilisin 168, subtilisin BPN', subtilisin Carlsberg, subtilisin DY, subtilisin 147 and subtilisin 309 (e.g., WO 1989/06279 and Stahl et al., 1984). In some embodiments of the present disclosure, the modified *Bacillus* cells produce mutant (i.e., variant) proteases. Numerous references provide examples of variant proteases, such as PCT Publication Nos. WO1999/20770; WO1999/20726; WO1999/20769; WO1989/06279; U.S. RE34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567 and 6,218,165. Thus, in certain embodiments, a modified *Bacillus* cells of the disclosure comprises an expression construct encoding a protease.

In certain other embodiments, a modified *Bacillus* cells of the disclosure comprises an expression construct encoding an amylase. A wide variety of amylase enzymes and variants thereof are known to one skilled in the art. For example, International PCT Publication NO. WO2006/037484 and WO 2006/037483 describe variant α-amylases having improved solvent stability, Publication No. WO1994/18314 discloses oxidatively stable α-amylase variants, Publication No. WO1999/19467, WO2000/29560 and WO2000/60059 disclose Termamyl-like α-amylase variants, Publication No. WO2008/112459 discloses α-amylase variants derived from *Bacillus* sp. number 707, Publication No. WO1999/43794 discloses maltogenic α-amylase variants, Publication No. WO1990/11352 discloses hyper-thermostable α-amylase variants, Publication No. WO2006/089107 discloses α-amylase variants having granular starch hydrolyzing activity.

In other embodiments, a POI or variant POI expressed and produced in a modified cell of the disclosure is a peptide, a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), variants thereof, fragments thereof and the like. Other types of proteins (or variants thereof) of interest may be those that are capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

There are various assays known to those of ordinary skill in the art for detecting and measuring activity of intracellularly and extracellularly expressed proteins. In particular, for proteases, there are assays based on the release of acid-soluble peptides from casein or hemoglobin measured as absorbance at 280 nm or colorimetrically, using the Folin method (e.g., Bergmeyer et al., 1984). Other assays involve the solubilization of chromogenic substrates (See e.g., Ward, 1983). Other exemplary assays include succinyl-Ala-Ala-Pro-Phe-para-nitroanilide assay (SAAPFpNA) and the 2,4,6-trinitrobenzene sulfonate sodium salt assay (TNBS assay). Numerous additional references known to those in the art provide suitable methods (See e.g., Wells et al., 1983; Christianson et al., 1994 and Hsia et al., 1999).

International PCT Publication No. WO2014/164777 discloses Ceralpha α-amylase activity assays useful for amylase activities described herein.

Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS).

EXAMPLES

Certain aspects of the present invention may be further understood in light of the following examples, which should not be construed as limiting. Modifications to materials and methods will be apparent to those skilled in the art. In addition, TABLE 1 presented below generally describes the *B. licheniformis* genetic modifications, growth phenotypes and the like, which are further described below in Examples 1-12.

TABLE 1

*B. licheniformis* Host Cells

| *B. licheniformis* Host Cell | Genotype | Genetic Modification | Growth Phenotype On Minimal Media | GOI Expressed |
|---|---|---|---|---|
| Host Cell 1 | Parental | N/A | Prototroph | N/A |
| Host Cell 2 | Daughter of Cell 1 | Transformed w/pBLcomK | Prototroph w/increased competency | N/A |
| Host Cell 3 | Daughter of Cell 2 | Δ lysA | Lysine auxotroph | N/A |
| Host Cell 4 | Daughter of Cell 3 | Δ lysA, pBLComK | Lysine auxotroph | N/A |
| Host Cell 5 | Daughter of Cell 4 | lysA restored | Prototroph | N/A |
| Host Cell 6 | Daughter of Cell 2 | Expressing α-amylase construct Host strain | Prototroph | N/A |
| Host Cell 7 | Daughter of Cell 4 | lysA-α-amylase construct [@ lysA locus] | Prototroph | α-amylase |
| Host Cell 8 | Daughter of Cell 4 | lysA-α-amylase construct [@ bofA locus] [@ amyL locus] [@ katE locus] [@ catH locus] [@ pdp locus] | Prototroph | α-amylase |
| Host Cell 9 | Daughter of Cell 2 | Partial Δ lysA-chloramphenicol | Lysine auxotroph | N/A |
| Host Cell 10 | Daughter of Cell 2 | 2-bp mutated lysA-chloramphenicol | Lysine auxotroph | N/A |
| Host Cell 11 | Daughter of Cell 2 | Δ serA | Serine auxotroph | N/A |
| Host Cell 12 | Daughter of Cell11 | Δ serA, pBLcomK | Serine auxotroph | N/A |
| Host Cell 13 | Daughter of Cell 9 | serA-α-amylase construct | Prototroph | α-amylase |
| Host Cell 14 | Daughter of Cell 2 | Δ pyrF-tet | Uracil auxotroph | N/A |
| Host Cell 15 | Daughter of Cell 4 | Δ lysA/Δ serA, pBLComK | Serine auxotroph Lysine auxotroph | N/A |
| Host cell 16 | Daughter of Cell 15 | lysA-α-amylase construct, pBLComK | Serine auxotroph | α-amylase |
| Host Cell 17 | Daughter of Cell 16 | lysA-α-amylase construct serA-α-amylase construct | Prototroph | α-amylase |
| Host Cell 18 | Ancestral strain | N/A | Prototroph | N/A |

Example 1

Lysine Auxotrophic *B. licheniformis* Cells and Methods Thereof

A lysine auxotrophic *Bacillus licheniformis* (daughter) host cell was obtained in the present example by deleting the complete lysA gene (SEQ ID NO: 1) in a parental *Bacillus licheniformis* host cell, which deletion included 67 bp upstream and 68 bp downstream of the lysA gene. More particularly, the lysA gene (SEQ ID NO: 1) of the parental *Bacillus licheniformis* host cell encodes the LysA protein comprising the amino acid sequence set forth in SEQ ID NO: 2. Thus, to engineer a lysA deletion, the upstream flanking region was amplified from the genomic DNA of the (parental) *B. licheniformis* host cell (HOST CELL 1) (using Q5® High-Fidelity DNA Polymerase (New England Bio-Labs, BIOKE, Leiden The Netherland), according to manufacturer's protocol, with an annealing temperature of 55° C. for 20 seconds and an elongation at 72° C. for 50 seconds, and primers forward primer 1 and reverse primer 1.

Forward primer 1:
(SEQ ID NO: 3)
GACGCGGCCGCCGATCAGGTCATTGCGAACG

Reverse primer 1:
(SEQ ID NO: 4)
TGCTCCTGCAGGCGGCTTCATGATAGTGCGAT

Additionally, the downstream flanking region of the lysA gene was amplified using forward primer 2 and reverse primer 2.

Forward primer 2:
(SEQ ID NO: 5)
CCGCCTGCAGGAGCACGAAAAACACTTCCCG

Reverse primer 2:
(SEQ ID NO: 6)
ATCCTCGAGATGGGTTCCGGCATACTTGT

After gel purification (BIOKE, Leiden The Netherland) of the amplicons, the purified upstream and downstream flanking amplicons were fused together by Q5® High-Fidelity DNA Polymerase fusion PCR amplification with primer forward primer 1 and reverse primer 2. The protocol used was as follows; 95° C. for 120 seconds, 10 cycles of [95° C. for 20 seconds, 70° C. for 1 second, ramp to 55° C. at 1° C./second, 55° C. for 30 seconds, 72° C. for 60 seconds], 5 cycles of [95° C. for 20 seconds, 70° C. for 1 second, ramp to 55° C. at 1° C./second, 55° C. for 30 seconds, 72° C. for 60 seconds, increase 5 seconds/cycle], 10 cycles of [95° C. for 20 seconds, 70° C. for 1 second, ramp to 55° C. at 1° C./second, 55° C. for 30 seconds, 72° C. for 80 seconds, increase 20 seconds/cycle], 72° C. for 180 seconds.

The fused amplicon was gel purified, followed by restriction digestion using "XhoI" and "NotI" (New England BioLabs, BIOKE, Leiden The Netherland) for 30 minutes at 37° C. The digested amplicon was gel purified and ligated into a "XhoI" and "NotI" digested and gel purified "pCZ105" (see, FIG. 1). The ligation was performed using the quick Ligation™ kit (1 hour 25° C.) (BIOKE, Leiden The Netherland), and the ligate was purified using the PCR cleanup kit (BIOKE, Leiden The Netherland). From the purified ligation, 5 ul was used for rolling circle amplification (18 hours, according to manufacturer's protocol; GE Healthcare Europe GmbH, Eindhoven, the Netherlands).

The rolling circle amplified ("RCA") mix of the pCZ105 plasmid harboring the fused up and downstream region of the lysA locus was transformed into competent (parental) *B. licheniformis* cells comprising (harboring) a pBLcomK plasmid (HOST CELL 2; see, FIG. 2) as generally described in International PCT Publication Nos. WO2017/075195, WO2002/14490 and WO2008/7989.

Formed colonies were inoculated in Luria broth containing 30 mg/l kanamycin and incubated overnight at 42° C. to promote single crossover integration in the genome, followed by plating on Luria agar containing 30 mg/l kanamycin. Single colonies were checked for correct integration in the genome using Platinum® Taq DNA Polymerase High Fidelity (Invitrogen, ThermoFisher Scientific, Breda, The Netherlands) (95-15 seconds, 55-15 seconds, 68-240 seconds) the following forward primer and reverse primer set forth below:

Forward primer 3:
(SEQ ID NO: 7)
CCAAGCGTCATCATCACACC

Reverse primer 3:
(SEQ ID NO: 8)
ACTCTTGCGTTCTTCTCCGT

Double crossover integration was obtained by culturing the correct single crossover integrants in Luria broth overnight at 37° C. followed by plating onto Luria agar. Colonies unable to grow in the presence of 30 mg/L Kanamycin were tested by PCR for double crossover integration using primers forward primer 3 and reverse primer 3. Correct clones were stored at −80° C. in 25% glycerol.

For verification of a lysine auxotrophy in the (daughter) *B. licheniformis* ΔlysA host cell (HOST CELL 3), four colonies of this strain, as well as (parental) *B. licheniformis* HOST CELL 1 was cultured in 20 mL Luria broth over night at 37° C. while shaking. The optical density at 600 nm of the grown cultures was measured the following day and the concentration of the cells was normalized to the lowest optical density of the strains. From these normalized cultures, 5 μl and a 10-fold and 100-fold dilution was spotted onto minimal M9 agar plates (13 g/l $Na_2HPO_4$-$7H_2O$, 3 g/l $KH_2PO_4$, 0.5 g/l NaCl, 1.0 g/l $NH_4Cl$, 20 g/l Bacto Agar, 2 ml of 1M $MgSO_4$, 100 μl of 1M $CaCl_2$ and 4 g/l glucose), with addition of 0, 10, 20, 30, 40, 50 μg/ml D-lysine. Plates were cultured for 48 hours at 37° C.

Figure 3:
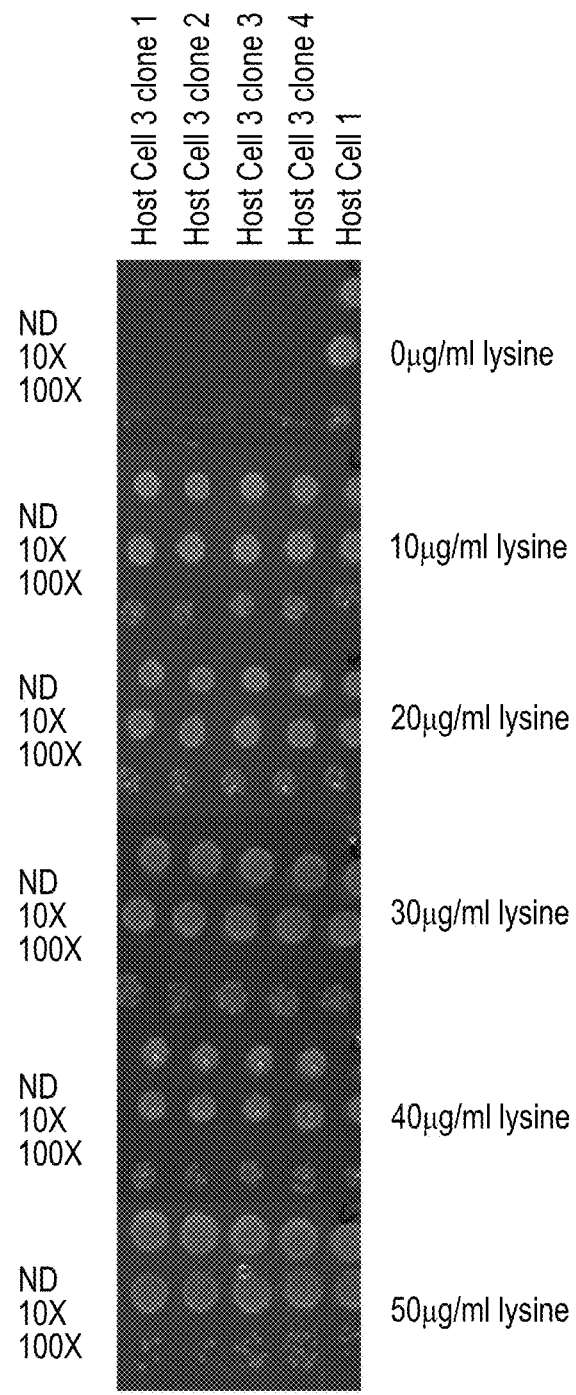
FIG. 3 shows the growth the (daughter) HOST CELL 3 colonies (i.e., HOST CELL 3, clones 1-4), and the HOST CELL 1 on minimal M9 agar medium containing 0-50 µg/ml of D-lysine, wherein "ND" is non-diluted, "10×" is 10 times diluted, "100×" is 100 times diluted, and 5 ul of culture was spotted onto the agar.

As shown in FIG. 3, the (daughter) HOST CELL 3 colonies (i.e., Host Cell 3, clones 1-4) showed no growth without addition of D-lysine, in contrast to the (parental) HOST CELL 1. Addition of 10-50 μg/ml D-lysine enabled growth in the HOST CELL 3 colonies. This result demonstrates that the engineered (daughter) HOST CELL 3 is lysine auxotrophic.

Example 2

Restoring Prototrophy in Lysine Auxotrophic *B. licheniformis* Cells and Methods Thereof To evaluate whether prototrophy of (daughter) *B. licheniformis* HOST CELL 3 described in Example 1 can be restored by re-introducing the lysA gene into the genome, the *B. licheniformis* HOST CELL 3 was transformed with the intact lysA gene and 1.3 kb flanks on either side of the lysA ORF This linear fragment was amplified using Q5® High-Fidelity DNA Polymerase, according to manufacturer's protocol, from a HOST CELL 1 using the following primers:

Forward primer 4:
(SEQ ID NO: 9)
CCAAGCGTCATCATCACACC

Reverse primer 4:
(SEQ ID NO: 10)
CGCCGAAACACCTCCTTTTT

In order to transform the *B. licheniformis* HOST CELL 3 with the amplified DNA, these cells were cultured to obtain protoplasts and re-transformed with the pBLComK plasmid (see, PCT International Publication Nos. WO2017/075195 and WO2005/111203).

Subsequently, the *B. licheniformis* ΔlysA host cell comprising pBLComK (HOST CELL 4) was made competent as described previously, wherein 3 μg of amplified linear product was added to HOST CELL 4 to promote double crossover integration of the amplicon in the genome, thereby restoring the LysA prototrophy, resulting in (daughter) HOST CELL 5. Water was also added to HOST CELL 4 as control transformation.

The following transformation protocol was used. From a single colony of a host cell containing pBLComK, a pure culture was made on LB 100 ppM spectinomycin. Using a single colony, a pre-culture shake flask with 25 ml of LB containing 100 mg/l spectinomycin was inoculated from this pre-culture and cultured overnight at 37° C. at 250 RPM using a 50 ml throw. From this pre-culture, the main culture was inoculated at OD600 of 0.7 (in duplicate) in 50 ml LB containing 100 mg/l spectinomycin. The main culture was performed in 250 ml baffled Erlenmeyer flasks and cultured at 37° C. at 250 RPM using a 50 ml throw. After the first hour of cultivation, 0.3% xylose was added to the culture broth. From mid culture grown cells 112.5 μl of culture broth was added to 12.5 μl of 100% DMSO and stored at −80° C. to be used for transformation. The transformation was followed by plating of the transformation mix onto minimal medium agar plates. Colony formation on the minimal M9 agar plates indicate the ability to of the cells to restore the lysA locus using the provided PCR amplicon of the intact lysA locus.

No colonies were observed on minimal M9 agar plates on the control (H₂O) transformation, indicating this strain remained LysA auxotrophic. The HOST CELL 4, transformed with 3 μg of PCR amplicon yielded colonies, thereby indicating this strain was prototrophic, wherein the lysA locus was restored (HOST CELL 5). For verification, the formed colonies were re-streaked onto minimal M9 agar plates and cultured overnight at 37° C. PCR was performed on these colonies, Q5® High-Fidelity DNA Polymerase, according to manufacturer's protocol, to verify the integration of the lysA gene into the correct locus by using primers inside the lysA gene, and outside the flanking regions of the lysA locus.

```
Forward primer 5:
                                    (SEQ ID NO: 11)
TTTAAGCCCGACGATCATCCA Reverse primer 5:
                                    (SEQ ID NO: 12)
GTGTTCCGTATCTTTCTGCCAA Forward primer 6:
                                    (SEQ ID NO: 13)
CTACAGCATGGCCAACAACTA Reverse primer 6:
                                    (SEQ ID NO: 14)
ATTTCAGAAAAGTCAGGCGGG
```

More particularly, as shown in FIG. 4A and FIG. 4B, both PCR amplifications yielded product (3.3 KB), indicating the lysA gene was correctly integrated in the correct locus, restoring the lysA gene in its original locus.

Example 3

Use of the lysA Gene as an Antibiotic-Free Selectable Marker and Methods Thereof In the instant example, the lysA gene was evaluated as a selectable marker in a LysA auxotrophic background (i.e., see *B. licheniformis* Host Cell 4) for expressing an α-amylase. More specifically, a linear construct was engineered, harboring on the 5' end a homology region to the lysA locus and the intact lysA gene, an α-amylase flanked by a promoter and terminator region, and a 3' homology region to the lysA locus. The 5' region and lysA gene were amplified from genomic DNA of HOST CELL 1, using Q5® High-Fidelity DNA Polymerase, according to manufacturer's protocol and forward/reverse primers 7:

```
Forward primer 7:
                                    (SEQ ID NO: 15)
GTGATGAAAAGGACCCAGGTGGCACTTTT

CGGGGAAATGTGCGCGGAACGCTTTGAC

CTTGGCGTACGGAAGGTC

Reverse primer 7:
                                    (SEQ ID NO: 16)
CCGAATTTTTAACAAGTACCATTTTCCCT

ATATTTTCTTCCAAAAGAAAAGCTGAATT

AAAAATGGAGACCCCCCTCTTAG
```

The α-amylase protein (an α-amylase variant described in PCT International Publication No. WO2017/100720), driven by a *B. licheniformis* endogenous promoter (LAT) and terminator (LAT), was amplified from the genomic DNA of a *B. licheniformis* host cell (i.e., HOST CELL 6) carrying the α-amylase expression cassette, using Q5® High-Fidelity DNA Polymerase, according to manufacturer's protocol and forward/reverse primers 8:

```
Forward primer 8:
                                    (SEQ ID NO: 17)
GGAAGAAAATATAGGGAAAATGGTACTTG

TTAAAAATTCGGAATATTTATACAATATC

ATATGACAGAATAGTCTTTTAAGTAAGTC

TAC

Reverse primer 8:
                                    (SEQ ID NO: 18)
AAAATAAAAAAACGGATTTCCTTCAGGAA

ATCCGTCCTCTCTGCTCTTTCATTGCTGC

ACCCATACTGAAACTG
```

The 3' homologous region was amplified from the genomic DNA of HOST CELL 1, using Q5® High-Fidelity DNA Polymerase, according to manufacturer's protocol and forward/reverse primers 9:

```
Forward primer 9:
                                    (SEQ ID NO: 19)
GAGCAGAGAGGACGGATTTCCTGAAGGAA

ATCCGTTTTTTATTTTCAAGCACGAAAA

ACACTTCCCGGTGATC

Reverse primer 9:
                                    (SEQ ID NO: 20)
GTGAAATACCGCACAGATGCGTAAGGAGA

AAATACCGCATCAGGAAATTGGTACAGCA

ATTCTGCCTGAAGCC
```

All fragments were gel purified and used in a fusion PCR amplification, using Q5® High-Fidelity DNA Polymerase, according to manufacturer's protocol, and forward primer 7 and reverse primer 10 (see, Example 4).

The PCR mix with the fused amplicon was transformed into pBLComK induced competent cells of HOST CELL 4 as described above. The transformed competent cells were plated onto M9 minimal agar medium containing 5 g/L Remazol brilliant blue R dried starch (RBB) (Sigma Aldrich, Zwijndrecht, the Netherlands) and culture for 48 hours at 37° C. Halo forming colonies were re-streaked onto fresh M9 minimal agar medium containing RBB.

Thus, the present example demonstrates the ability of the *B. licheniformis* transformant strain to grow in absence of exogenous lysine, wherein the lysine auxotrophy of HOST CELL 4 was restored after transformation. Additionally, the activity of the introduced α-amylase variant was confirmed using a Ceralpha α-amylase assay (Megazyme, Wicklow, Ireland), indicating the functional expression of a gene of interest (GOI) in the lysA locus using lysA as a marker.

Example 4

Use of the lysA Gene as an Antibiotic-Free Selectable Marker Outside of the lysA Genomic Locus and Methods Thereof The present example describes the use of the lysA gene as an antibiotic-free selectable marker outside of the lysA locus. More specifically, a linear construct was engineered expressing an α-amylase variant described in Example 3, to be expressed in *B. licheniformis* cells with the lysA gene in the bofA locus, as well as the amyL locus. The upstream region of the bofA locus and the lysA gene (including the promoter region and the downstream region of bofA) was amplified from genomic DNA of HOST CELL 1, using Q5® High-Fidelity DNA Polymerase, according to manufacturer's protocol and primers:

```
bofA upstream Forward primer 10:
                                  (SEQ ID NO: 21)
GTGATGAAAAGGACCCAGGTGGCACTTTT

CGGGGAAATGTGCGCGGAACGTTGGGGAC

AATTGCTTGCCCAGCTGAAAC bofA upstream Reverse primer 10:
                                  (SEQ ID NO: 22)
GAGCCGAAAAGCTGAGATTTTCGCGACTATA

ATATCTTAACATTTAATCGTGATGTC lysA gene and promoter region:
Forward primer 11:
                                  (SEQ ID NO: 23)
GACATCACGATTAAATGTTAAGATATTATAG

TCGCGAAAATCTCAGCTTTTCGGCTC

Reverse primer 11:
                                  (SEQ ID NO: 24)
CCGAATTTTTAACAAGTACCATTTTCCCTA

TATTTTCTTCCAAAAGAAAAGCTGAATTAA

AAATGGAGACCCCCCTCTTAG

The bofA downstream region:
Forward primer 12:
                                  (SEQ ID NO: 25)
```
GAGCAGAGAGGACGGATTTCCTGAAGGAAA

TCCGTTTTTTTATTTTGCTTTGAGAGCGGC

AACGAAGTTC

```
Reverse primer 12:
                                  (SEQ ID NO: 26)
GTGAAATACCGCACAGATGCGTAAGGAGA

AAATACCGCATCAGGAAATTGGGCCGTAT

TGAGCTTCGGCATCTCGG
```

The α-amylase variant was amplified from genomic DNA of HOST CELL 6 using primers forward and reverse primers 8 (SEQ ID NOs: 17 and 18; see Example 3) and Q5® High-Fidelity DNA Polymerase, according to manufacturer's protocol. The four (4) fragments obtained were fused together into one linear fragment using forward primer 10 (SEQ ID NO: 21) and reverse primer 12 (SEQ ID NO: 26), followed by transformation of pBLComK induced competent cells of HOST CELL 4 as described above.

The transformed competent cells were plated onto M9 minimal agar medium containing 5 g/L Remazol brilliant blue R dried starch (RBB) (Sigma Aldrich, Zwijndrecht, the Netherlands) and cultured for 48 hours at 37° C. Halo forming colonies were re-streaked onto fresh M9 minimal agar medium containing RBB.

Thus, the present example demonstrates the ability of the *B. licheniformis* transformant strain to grow in absence of exogenous lysine, and as such, the lysine auxotrophy of HOST CELL 4 was restored after transformation with the lysA gene (including the promoter region) which was introduced in a different locus of the *B. licheniformis* genome. Moreover, four (4) loci, the amyL locus, katE locus, pdp locus region and the catH locus, were used for integration a gene of interest (GOI) using the lysA gene as a selectable marker, all yielding the same results as described above. The activity of the introduced α-amylase variant was confirmed using a Ceralpha α-amylase assay (Megazyme, Wicklow, Ireland), indicating the functional expression of the GOI when using the lysA gene as a marker outside of its original (lysA) locus.

Example 5

Lysine Auxotrophic *B. licheniformis* Cells Comprising a Partial Deletion of the lysA Locus To evaluate whether a partial deletion of the lysA locus could render the *B. licheniformis* strain auxotrophic for lysine, a linear construct was engineered with the upstream flanking region of the lysA locus and the lysA locus without 307 bp, which was fused to a chloramphenicol marker (SEQ ID NO: 69) and to the downstream flanking region of the lysA locus. The following primers and Q5® High-Fidelity DNA Polymerase, according to manufacturer's protocol were used on genomic DNA of HOST CELL 1 and on an ancestral *B. licheniformis* strain (chloramphenicol marker):

```
Upstream flanking region:
Forward primer 13:
                                  (SEQ ID NO: 29)
TACAGCATTTCGCGGCCGTAC Reverse primer 13:
                                  (SEQ ID NO: 30)
CATAGATCGGGGTGAAGATGTCATGATCTT

ATTTTGCCTCATAAAGCGCCGGCCTG
```

The chloramphenicol marker:
Forward primer 14:
(SEQ ID NO: 31)
CAGGCCGGCGCTTTATGAGGCAAAATAAGA

TCATGACATCTTCACCCCGATCTATG

Reverse primer 14:
(SEQ ID NO: 32)
ATTAGCCCGGTCGCTGTTCTATGCATTTA

AGAGACCCGCTAAGAAGTACATA

The downstream lysA flanking region:
Forward primer 15:
(SEQ ID NO: 33)
TATGTACTTCTTAGCGGGTCTCTTAAATGC

ATAGAACAGCGACCGGGCTAAT

Reverse primer 15:
(SEQ ID NO: 34)
GTTCAGACACACAATATCAGCAG

All fragments were used in fusion PCR using primer forward 13 and reverse 15. The resulting linear fragment was transformed into HOST CELL 2 and colonies were streaked onto HI containing 7.5 ppm chloramphenicol. After genome sequence verification of the engineered strain, this strain was streaked onto M9 minimal medium and M9 minimal medium containing 50 ppm lysine and cultured at 37° C. for 96 hours. Colonies only appeared on the M9 minimal medium plates containing lysine, indicating that the partial deletion of the lysA gene induces lysine auxotrophy. A single colony was stocked at ⁻80° C. (HOST CELL 9).

Example 6

Lysine Auxotrophic B. licheniformis Cells Comprising a Mutated lysA Locus

To evaluate the use of a mutated lysA locus as a selectable auxotrophic marker, a synthetic lysA gene was ordered, including 577 bp upstream of the lysA locus. The synthetic lysA gene has a deletion of one (1) bp at position 501 and at position 845. This fragment was amplified from the synthetic construct using Q5® High-Fidelity DNA Polymerase, according to manufacturer's protocol and forward/reverse primers 16:

Forward primer 16:
(SEQ ID NO: 35)
GGAAATGTGCGCGGAACCCCTATTTG

CATTTCGCGGCCGTACGGGTCAATCG

Reverse primer 16:
(SEQ ID NO: 36)
ATACTGACATAGATCGGGGTGAAGAT

GTCATGATCTTTTTAACAAAAAACAC

Additionally, a linear fragment containing the chloramphenicol marker and promoter region was amplified from genomic DNA of an ancestral B. licheniformis host strain using forward/reverse primers 17:

Forward primer 17:
(SEQ ID NO: 37)
GTGTTTTTTGTTAAAAAGATCATGAC

ATCTTCACCCCGATCTATGTCAGTAT

Reverse primer 17:
(SEQ ID NO: 38)
ATTAGCCCGGTCGCTGTTCTATGCAT

TTAAGAGACCCGCTAAGAAGTACATA

A linear fragment containing the downstream flanking region of the lysA locus was also amplified from the genomic DNA of HOST CELL 1 using forward/reverse primers 18:

Forward primer 18:
(SEQ ID NO: 39)
TATGTACTTCTTAGCGGGTCTCTTAA

ATGCATAGAACAGCGACCGGGCTAAT

Reverse primer 18:
(SEQ ID NO: 40)
AGATGCGTAAGGAGAAAATACCGCAT

GGAGGGCATTTGACTTGAAGAGAAAA

All fragments were gel purified and used as template in a fusion PCR with the following primers:

Forward primer 19:
(SEQ ID NO: 41)
GTCAATCGTTGACGAATGAAGG

Reverse primer 20:
(SEQ ID NO: 42)
GGCATTTGACTTGAAGAGAAAATTCTC

Figure 5:
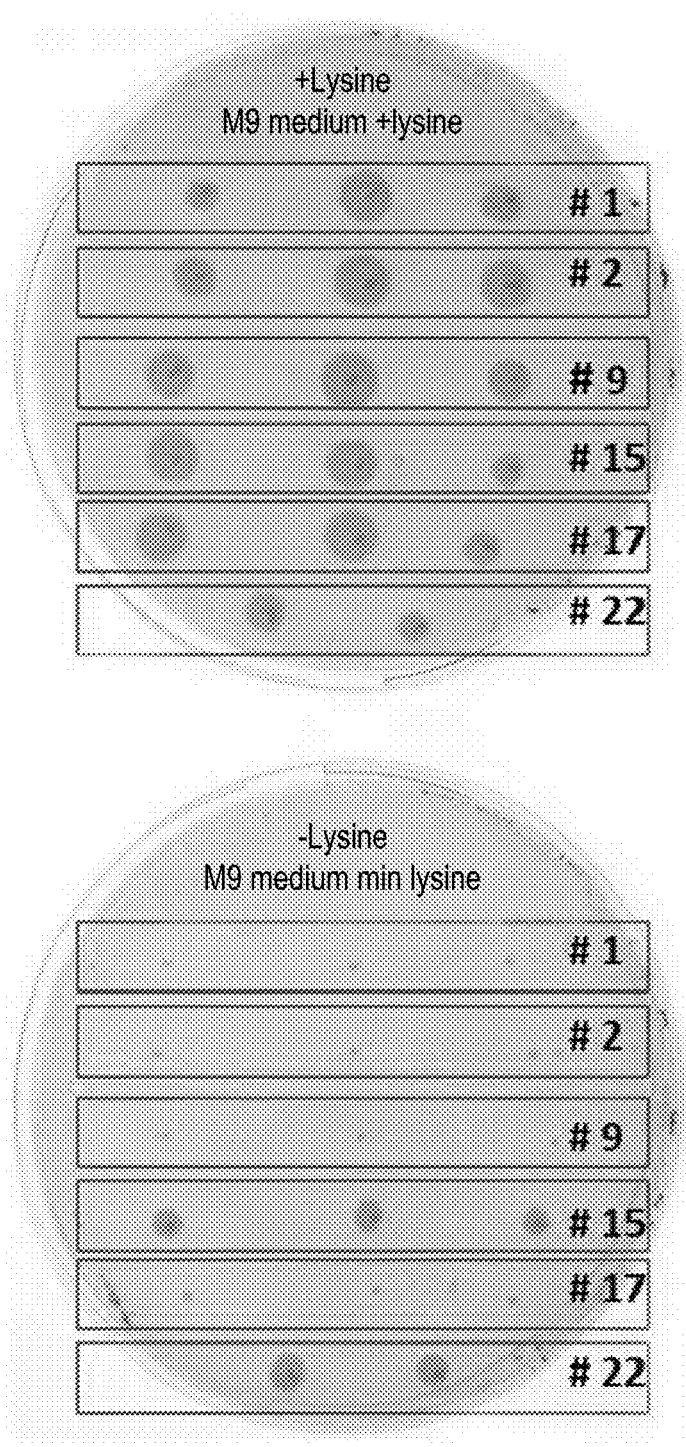
FIG. 5 shows a plate containing M9 minimal agar medium containing 50 ppm lysine (FIG. 5, upper photograph) and a plate containing M9 minimal agar medium (FIG. 5, lower photograph). The six (6) colonies were patched onto both plates after transformation and pick and patching onto HI agar containing 7.5 ppm chloramphenicol. Four (4) out of six (6) colonies patched clearly show an auxotrophic lysine phenotype.

The complete fusion PCR mix was transformed into competent HOST CELL 2, as described above and plated onto HI agar plates containing 7.5 ppm chloramphenicol and cultured at 37° C. Formed colonies were picked and patched onto fresh HI agar plates containing 7.5 chloramphenicol. To verify if the formed colonies were lysine auxotrophic, the colonies were picked and patched onto M9 minimal agar medium with and without 50 ppm lysine. As presented in FIG. 5, four (4) out of six (6) colonies patched (FIG. 5, lower photograph; colonies #1, #2, #9 and #17) showed clear auxotrophy for lysine, demonstrating that two (2) single base pair deletions render the strain auxotrophic for lysine. A single colony was stocked at ⁻80° C. (HOST CELL 10).

Example 7

Serine Auxotrophic B. licheniformis Cells and Methods Thereof

A serine auxotrophic Bacillus licheniformis (daughter) host cell was obtained in the present example by deleting the complete serA gene in a parental Bacillus licheniformis host cell. More particularly, the serA gene (SEQ ID NO:27), coding for the SerA protein (SEQ ID NO: 28), including 63 bp upstream (and excluding 44 bp 3' of the gene) was deleted in a B. licheniformis host cell. To engineer a serA deletion, the upstream flanking region was amplified from the genomic DNA of a B. licheniformis host cell (HOST CELL 1) (using Q5® High-Fidelity DNA Polymerase (New England BioLabs, BIOKE, Leiden The Netherland), according to manufacturer's protocol, with an annealing temperature of 55° C. for 20 seconds and an elongation at 72° C. for 50 seconds, and the following forward/reverse primers 21:

```
Forward primer 21:
                                        (SEQ ID NO: 43)
GATGCGGCCGCATCGAAACGGCCATCACAAG Reverse primer 21:
                                        (SEQ ID NO: 44)
GGATGTCCTGCAGGGTCAATGAGTTTCACGCGGAA
```

Additionally, the downstream flanking region of the serA gene was amplified using forward/reverse primers 22:

```
Forward primer 22:
                                        (SEQ ID NO: 45)
ATTGACCCTGCAGGACATCCCGGATATCGTGTCT Reverse primer 22:
                                        (SEQ ID NO: 46)
ATGCTCGAGCGGAAGCCTCAGAGTGGATT
```

After gel purification (BIOKE, Leiden The Netherland) of the amplicons, the purified upstream and downstream flanking amplicons were fused together by Q5® High-Fidelity DNA Polymerase fusion PCR amplification with primer forward primer 21 and reverse primer 22 and the protocol described above.

The fused amplicon was gel purified, followed by restriction digestion using "XhoI" and "NotI" (New England BioLabs, BIOKE, Leiden The Netherland) for 30 minutes at 37° C. The digested amplicon was gel purified and ligated into a "XhoI" and "NotI" digested and gel purified "pCZ105" (see, FIG. 1). The ligation was performed using the quick Ligation™ kit (1 hour 25° C.) (BIOKE, Leiden The Netherland), and the ligate was purified using the PCR cleanup kit (BIOKE, Leiden The Netherland). From the purified ligation, 5 ul was rolling circle amplified (18 hours, according to manufacturer's protocol (GE Healthcare Europe GmbH, Eindhoven, the Netherlands).

The rolling circle amplified ("RCA") mix of the pCZ105 plasmid harboring the fused up and downstream region of the serA locus was transformed into competent *B. licheniformis* HOST CELL 2. Single crossovers and double crossovers were obtained as described above. The obtained *B. licheniformis* with a deleted serA gene (HOST CELL 11) was transformed with the pBLcomK plasmid as described above, yielding HOST CELL 12.

Plating of HOST CELL 12 and the wild type HOST CELL 1 onto M9 minimal agar medium and on M9 minimal agar medium supplemented with 50 ppm serine, yielded colonies on all plates for HOST CELL 1. However, for HOST CELL 12, colonies were only observed when serine was supplemented, indicating the serine auxotrophy of the serA deleted strain.

Example 8

Use of the serA Gene as an Antibiotic-Free Selectable Marker and Methods Thereof In the instant example, the serA gene was evaluated as a selectable marker in a SerA auxotrophic background for expressing an α-amylase gene of interest. More particularly, the serine auxotrophic *B. licheniformis* host cell (i.e., Host Cell 12) described above in Example 7 was used to express an α-amylase of interest, wherein a linear construct was engineered harboring on the 5' flank of the serA locus, an α-amylase flanked by a promoter and terminator region and a 3' homology region (which included the intact serA gene and promoter region). The 5' flanking region and 3' flanking region with the serA gene was amplified from genomic DNA of HOST CELL 1, using Q5® High-Fidelity DNA Polymerase, according to manufacturer's protocol and primers

```
5' flanking region:
Forward primer 23:
                                        (SEQ ID NO: 47)
CGGGGAAATGTGCGCGGAACCCCTAT

TTGCTCTGACCAAAGACTCCTGCTTC

Reverse primer 23:
                                        (SEQ ID NO: 48)
GTCAGCTGTTTATCAGCGAGAGCTCG

GAAAAAGTGAGTTTACCGAAATATC

3' region:
Forward primer 24:
                                        (SEQ ID NO: 49)
CATATTCCGCATTCGCAATGCCTACC

GCATACTAAAAACCGCACATTCACAG

Reverse primer 24:
                                        (SEQ ID NO: 50)
CAGATGCGTAAGGAGAAAATACCGCA

TATGCTGATCACTCCCCAGTTAATCG
```

The α-amylase variant (described in PCT Publication No. WO2017/100720) was amplified from genomic DNA of HOST CELL 6 using primers:

```
Forward primer 25:
                                        (SEQ ID NO: 51)
GATATTTCGGTAAACTCACTTTTTCCG

AGCTCTCGCTGATAAACAGCTGAC

Reverse primer 25:
                                        (SEQ ID NO: 52)
CTGTGAATGTGCGGTTTTTAGTATGCG

GTAGGCATTGCGAATGCGGAATATG
```

All fragments were assembled using fusion PCR with Q5® High-Fidelity DNA Polymerase, according to manufacturer's protocol and primers:

```
Forward primer 26:
                                        (SEQ ID NO: 53)
GCTTCAATCGTTGAACGCTGGC Reverse primer 26:
                                        (SEQ ID NO: 54)
CAGTTAATCGAACAGATCAGATCTC
```

The fusion PCR mix was transformed into competent HOST CELL 12 and plated onto M9 minimal agar medium, containing 5 g/L Remazol brilliant blue R dried starch (RBB) (Sigma Aldrich, Zwijndrecht, the Netherlands), and cultured at 37° C. After picking and patching halo forming colonies onto fresh M9 minimal agar medium plates, the activity of the introduced α-amylase variant was confirmed using a Ceralpha α-amylase assay (Megazyme, Wicklow, Ireland), indicating the functional expression of an α-amylase (GOI) in the serA locus using serA as a selectable marker. Additionally, a single colony was stocked at −80° C. (HOST CELL 13).

Example 9

Uracil Auxotrophic B. licheniformis Cells and Methods Thereof

An uracil auxotrophic *Bacillus licheniformis* (daughter) host cell was obtained in the present example by mutating the pyrF gene in a parental *Bacillus licheniformis* host cell. More particularly, a synthetic linear fragment comprising 427 bp upstream of the pyrF and pyrE gene and 102 bp downstream of pyrE gene. The pyrF gene comprised two (2) base pair deletions at position 538 and 563. This fragment was PCR amplified from the synthetic fragment using primers:

```
Forward primer 27:
                              (SEQ ID NO: 55)
GGAAATGTGCGCGGAACCCCTATTTG

GTCTATGTGAAGCTGTCGCCGAACGT

Reversed primer 27:
                              (SEQ ID NO: 56)
AACAATATGGCCCGTTTGTTGAACTG

GGATTAATAAAAAATAAAAATAATCC
```

Additionally, a tetracycline marker and promoter region was amplified from synthetically ordered sequence (SEQ ID NO: 69) using primers:

```
Forward primer 28:
                              (SEQ ID NO: 57)
GGATTATTTTTATTTTTATTAATCC

CAGTTCAACAAACGGGCCATATTGTT

Reversed primer 28:
                              (SEQ ID NO: 58)
TAAAAGTCAACCCGACTTTTTTATA

GCCGCGCATAAAAAAAGACCATTCCT
```

The downstream flanking region of the pyrE locus was amplified using primer:

```
Forward primer 29:
                              (SEQ ID NO: 59)
AGGAATGGTCTTTTTTTATGCGCGGC

TATAAAAAAAGTCGGGTTGACTTTTA

Reversed primer 29:
                              (SEQ ID NO: 60)
AGATGCGTAAGGAGAAAATACCGCATG

ACTCATCTCCTTACTCGTGTAATCC
```

The three fragments were gel purified and used in a fusion PCR with the following primers:

```
Forward primer 30:
                              (SEQ ID NO: 61)
CATTACCGACATCGCTCTTGC Reversed primer 30:
                              (SEQ ID NO: 62)
CTCCTTACTCGTGTAATCCGCATTC
```

Figure 6:
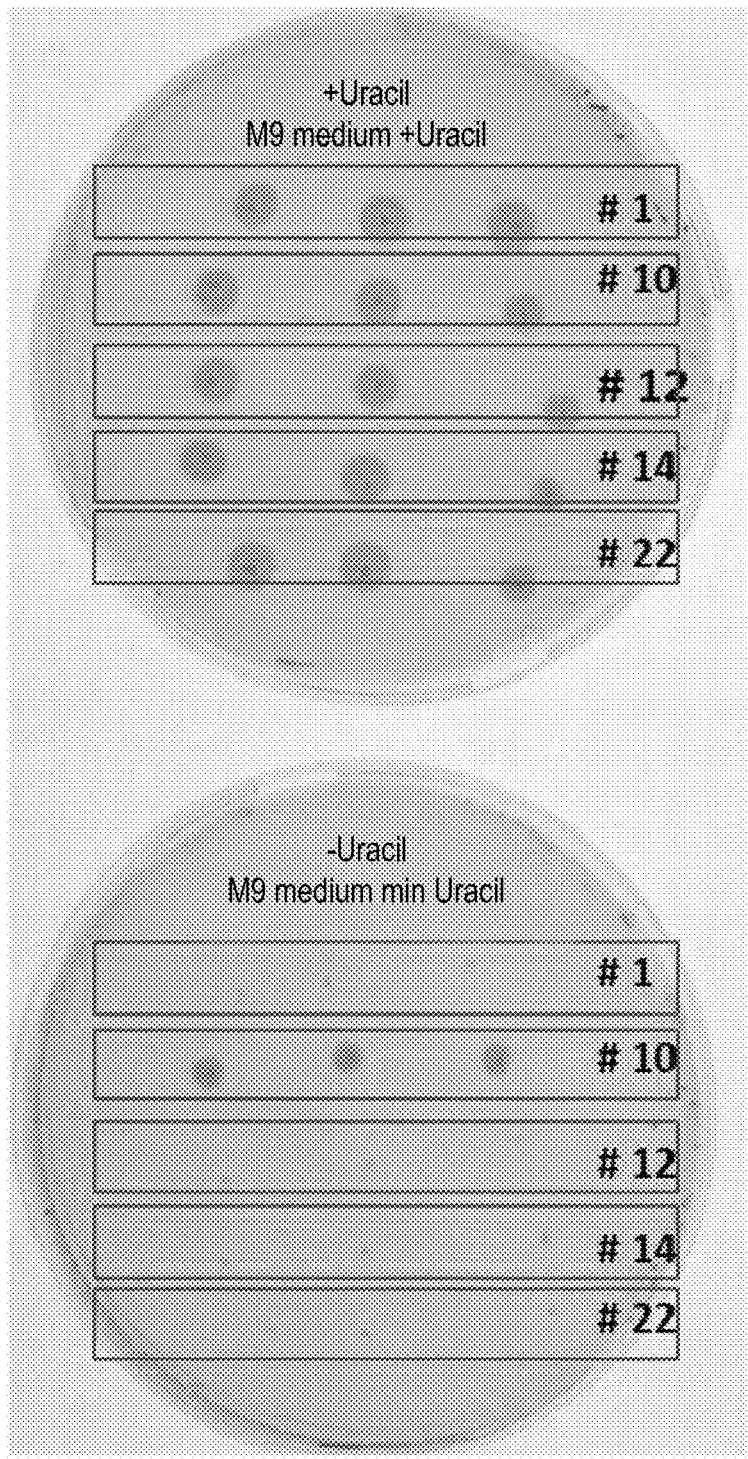
FIG. 6 shows a plate containing M9 minimal agar medium containing 50 ppm uracil (FIG. 6, upper photograph) and a plate containing M9 minimal agar medium (FIG. 6, lower photograph). Five (5) colonies were patched onto both plates after transformation and pick and patching onto HI agar containing 10 ppm tetracycline. Four (4) out of five (5) colonies patched clearly show an auxotrophic uracil phenotype.
Figure 8:
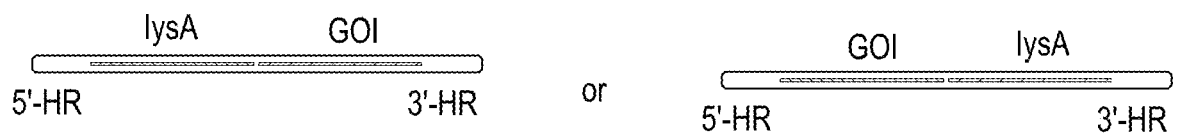
FIG. 8 shows schematic diagrams of certain exemplary DNA constructs encoding a gene of interest (G01), wherein Schematic I shows lysA constructs, Schematic II shows serA constructs and Schematic III shows pyrF constructs. "5' HR" and "3' HR" are (*B. licheniformis*) 5' and 3' homology regions, "lysA", "serA" and "pyrF" indicate genes encoding selectable markers LysA, SerA and PyrF, respectively, and "GOI" indicates a gene of interest encoding a protein of interest.
Figure 8:
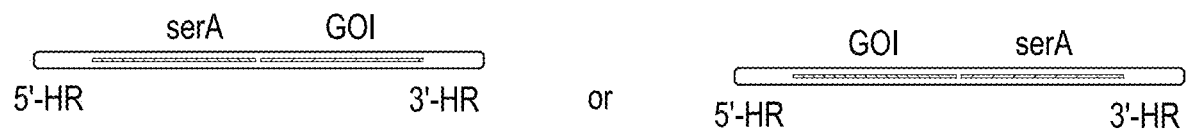
Figure 8:
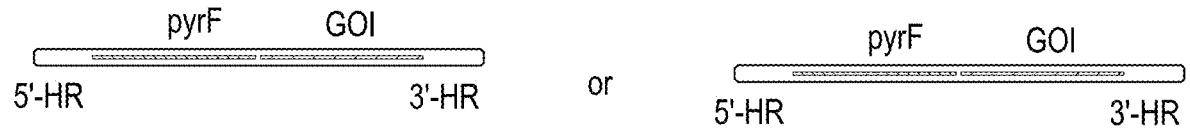

The complete fusion PCR mix was transformed into competent *B. licheniformis* cells (i.e., HOST CELL 2) and plated onto HI agar containing 10 ppm tetracycline (Sigma Aldrich, Zwijndrecht, the Netherlands). After picking and patching of the formed colonies onto fresh HI agar containing 10 ppm tetracycline, the colonies were validated for their uracil auxotrophy, wherein five (5) colonies were picked and patched onto M9 minimal agar medium with and without 50 ppm uracil. As is shown in FIG. 6, four (4) out of five (5) colonies patched were unable to grow in absence of uracil (FIG. 6, lower photograph; colonies #1, #12, #14 and #22). This result demonstrates that an uracil auxotrophic phenotype was obtained in the *B. licheniformis* strain comprising the two base pair deletions. A single colony was stocked at $^-80°$ C. degrees (HOST CELL 14).

Example 10

B. licheniformis Cells Comprising Multiple Selectable Auxotrophic Markers and Methods Thereof The present example evaluates the use of multiple auxotrophic markers in a single *B. licheniformis* host cell. For example, a *B. licheniformis* host comprising a deleted lysA locus and a deleted serA locus in the same host (comprising pBLComK plasmid; i.e., HOST CELL 15) was used to express two (2) copies of an α-amylase gene. The host was engineered by sequential deletion of the lysA and the serA gene as described above. First a linear construct of the α-amylase variant (as described in ABC123, driven by an endogenous promoter (LAT) and terminator (LAT), together with the complete lysA locus and promoter region was transformed into competent HOST CELL 15.

Positive halo forming colonies were identified on M9 minimal medium containing 5 g/L RBB and 50 ppm serine. After picking and patching onto fresh onto M9 minimal medium containing 5 g/L RBB, 50 ppm serine and 100 ppm spectinomycin (for pBLcomK plasmid retention), and sequence verification of the integrated region, a colony (HOST CELL 16) was grown for competence as described previously. A linear construct of an additional copy of the α-amylase variant gene, driven by an endogenous promoter (LAT) and terminator (LAT) and the serA locus and promoter region was transformed in HOST CELL 16. Halo forming colonies were picked on M9 minimal medium containing 5 g/L RBB and checked by PCR for the integration of the second copy of the α-amylase variant using the following primers and Q5® High-Fidelity DNA Polymerase, according to manufacturer's protocol.

```
Forward primer 31:
                              (SEQ ID NO: 63)
GCTTCAATCGTTGAACGCTGGC Reverse primer 31:
                              (SEQ ID NO: 64)
CTGACGGAAAATTGGTGCAGAC
```

Colonies yielding positive results from this PCR were additionally verified by genome sequencing. Clones were obtained with the correct integration of both copies of the α-amylase using lysA locus and serA locus, prototrophic for both lysine and serine amino acids, and active copies of α-amylase variant. A single colony was stocked at −80° C. (HOST CELL 17). Thus, these results demonstrate the effective use of multiple selectable auxotrophic markers for expressing multiple active copies of a gene of interest in a *B. licheniformis* host cell.

Example 11

Use of the lysA and serA Gene as an Antibiotic-Free Selectable Marker and Methods Thereof In the instant example, the lysine auxotrophic *B. licheniformis* host cell (i.e., Host Cell 4) described above in Example 3 is used to clone and express a protease of interest, wherein a linear construct harboring on the 5' end a homology region (5' HR) to the lysA locus and the intact lysA gene, a gene encoding the protease of interest flanked by a promoter and transcription terminator, and a 3' homology region (3' HR) to the lysA locus is used.

Following transformation of this DNA construct into HOST CELL 4 and plating onto M9 minimal agar medium and culturing for 24 hours at 37° C., transformants are picked that are prototrophic for lysine and produce the protease of interest. A similar strategy is used to introduce a copy of the protease gene into the ΔserA locus of e.g., Host Cell 12 by using serA and flanking sequences and selection for serine prototrophy. By using double (e.g. ΔlysA, ΔserA), triple (e.g. ΔlysA, ΔserA, ΔpyrF), quadruple, etc. auxotrophic strains, multiple copies of the gene encoding the protease of interest can be introduced into *Bacillus* host cells.

Example 12

Auxotrophic *B. licheniformis* Cells and Improved Transformation Efficiency

The present example evaluates *B. licheniformis* transformation efficiencies using linear DNA constructs of the disclosure, wherein an auxotrophic *B. licheniformis* strain is transformed with a linear DNA fragment comprising a lysA marker. In order to compare competence difference (e.g., via transformation efficiency) between *B. licheniformis* HOST CELL 4 (i.e., transformed with a linear fragment comprising a lysA marker) relative to *B. licheniformis* HOST CELL 2 (i.e., transformed with a linear fragment comprising a chloramphenicol marker). the linear fragment comprising the lysA marker was engineered as described in Example 2. Likewise, a linear DNA fragment comprising a chloramphenicol marker t was engineered by PCR amplification on the genomic DNA of HOST CELL 18, using Q5 polymerase and primers:

```
Forward primer 32:
                              (SEQ ID NO: 72)
TGCCCCTCTATTCTGAAACCG Reverser primer 32:
                              (SEQ ID NO: 73)
ACCTTCCTTTATGCTTTCGACG
```

More particularly, the resulting linear fragments were gel purified and used in the transformation procedure. For example, (a) the linear fragment comprising the lysA marker was transformed into competent HOST CELL 4, and plated onto M9 minimal agar medium, and (b) the linear fragment comprising the chloramphenicol marker was transformed at equal concentrations (i.e., relative to the linear fragment comprising lysA) into competent HOST CELL 2, and plated onto HI agar containing 7.5 ppm CMP. After seventy-two (72) hours of cultivation, a 100 fold higher CFU count was observed on the M9 minimal agar plate with the HOST CELL 4 transformed with the lysA marker. This result indicates that a higher transformation efficiency is observed when using an auxotrophic marker.

REFERENCES

PCT International Publication No. WO1989/06279
PCT International Publication No. WO1990/11352
PCT International Publication No. WO1994/18314
PCT International Publication No. WO1999/19467
PCT International Publication No. WO1999/20726
PCT International Publication No. WO1999/20769
PCT International Publication No. WO1999/20770
PCT International Publication No. WO1999/43794
PCT International Publication No. WO2000/39560
PCT International Publication No. WO2000/60059
PCT International Publication No. WO2001/51643
PCT International Publication No. WO2002/14490
PCT International Publication No. WO2003/083125
PCT International Publication No. WO2003/089604
PCT International Publication No. WO2005/111203
PCT International Publication No. WO2006/037483
PCT International Publication No. WO2006/037484
PCT International Publication No. WO2006/089107
PCT International Publication No. WO2008/112459
PCT International Publication No. WO2014/164777
PCT International Publication No. WO2017/075195
PCT International Publication No. WO2017/100720
U.S. Pat. No. 4,914,031
U.S. Pat. No. 4,980,288
U.S. Pat. No. 5,208,158
U.S. Pat. No. 5,310,675
U.S. Pat. No. 5,336,611
U.S. Pat. No. 5,399,283
U.S. Pat. No. 5,441,882
U.S. Pat. No. 5,482,849
U.S. Pat. No. 5,631,217
U.S. Pat. No. 5,665,587
U.S. Pat. No. 5,700,676
U.S. Pat. No. 5,741,694
U.S. Pat. No. 5,858,757
U.S. Pat. No. 5,880,080
U.S. Pat. No. 6,197,567
U.S. Pat. No. 6,218,165
U.S. RE 34,606
Bergmeyer et al., "*Methods of Enzymatic Analysis*" vol. 5, *Peptidases, Proteinases and their Inhibitors*, Verlag Chemie, Weinheim, 1984.
Botstein and Shortie, *Science* 229: 4719, 1985.
Brode et al., "Subtilisin BPN' variants: increased hydrolytic activity on surface-bound substrates via decreased surface activity", *Biochemistry*, 35(10):3162-3169, 1996.
Caspers et al., "Improvement of Sec-dependent secretion of a heterologous model protein in *Bacillus subtilis* by saturation mutagenesis of the N-domain of the AmyE signal peptide", *Appl. Microbiol. Biotechnol.*, 86(6):1877-1885, 2010.
Chang et al., *Mol. Gen. Genet.*, 168:11-115, 1979.
Christianson et al., *Anal. Biochem.*, 223:119-129, 1994.
Devereux et at, *Nucl. Acid Res.*, 12: 387-395, 1984.
Earl et al., "Ecology and genomics of *Bacillus subtilis*", *Trends in Microbiology.*, 16(6): 269-275, 2008.
Ferrari et al., "*Genetics*," in Harwood et al. (ed.), *Bacillus*, Plenum Publishing Corp., 1989.
Fisher et. al., *Arch. Microbiol.*, 139:213-217, 1981.
Hamoen et al., "Controlling competence in *Bacillus subtilis*: shared used of regulators", *Microbiology*, 149:9-17, 2003.

Hamoen et al., *Genes Dev.* 12:1539-1550, 1998.
Hardwood and Cutting (eds.) *Molecular Biological Methods for Bacillus*, John Wiley & Sons, 1990.
Higuchi et al., *Nucleic Acids Research* 16: 7351, 1988.
Ho et al., *Gene* 77: 61, 1989.
Hoch et al., *J. Bacteriol.*, 93:1925-1937, 1967.
Holubova, *Folia Microbiol.*, 30:97, 1985.
Hopwood, *The Isolation of Mutants in Methods in Microbiology* (J. R. Norris and D. W. Ribbons, eds.) pp 363-433, Academic Press, New York, 1970.
Horton et al., *Gene* 77: 61, 1989.
Hsia et al., *Anal Biochem.*, 242:221-227, 1999.
Iglesias and Trautner, *Molecular General Genetics* 189: 73-76, 1983.
Jensen et al., "Cell-associated degradation affects the yield of secreted engineered and heterologous proteins in the *Bacillus subtilis* expression system" *Microbiology*, 146 (Pt 10:2583-2594, 2000.
Liu and Zuber, "A molecular switch controlling competence and motility: competence regulatory factor ComS, MecA and ComK control signma-dependent gene expression in *Bacillus subtilis*", *J. Bacteriol.* 180(16): 4253-4251, 1998.
Lo et al., *Proceedings of the National Academy of Sciences USA* 81: 2285, 1985.
Mann et al., *Current Microbiol.*, 13:131-135, 1986.
McDonald, *J. Gen. Microbiol.*, 130:203, 1984.
Needleman and Wunsch, *J. Mol. Biol.*, 48: 443, 1970.
Olempska-Beer et al., "Food-processing enzymes from recombinant microorganisms—a review'" *Regul. Toxicol. Pharmacol.*, 45(2):144-158, 2006.
Palmeros et al., *Gene* 247:255-264, 2000.
Parish and Stoker, *FEMS Microbiology Letters* 154: 151-157, 1997.
Pearson and Lipman, *Proc. Natl. Acad. Sci. USA* 85: 2444, 1988.
Perego, 1993, In A. L. Sonneshein, J. A. Hoch, and R. Losick, editors, *Bacillus subtilis and Other Gram-Positive Bacteria*, Chapter 42, *American Society of Microbiology*, Washington, D.C.
Raul et al., "Production and partial purification of alpha amylase from *Bacillus subtilis* (MTCC 121) using solid state fermentation", *Biochemistry Research International*, 2014.
Sarkar and Sommer, *BioTechniques* 8: 404, 1990.
Saunders et al., *J. Bacteriol.*, 157:718-726, 1984.
Shimada, *Meth. Mol. Biol.* 57: 157; 1996.
Smith and Waterman, *Adv. Appl. Math.*, 2: 482, 1981.
Smith et al., *Appl. Env. Microbiol.*, 51:634 1986.
Stahl and Ferrari, *J. Bacteriol.*, 158:411-418, 1984.
Tarkinen, et al, *J. Biol. Chem.* 258: 1007-1013, 1983.
Van Dijl and Hecker, "*Bacillus subtilis*: from soil bacterium to super-secreting cell factory", *Microbial Cell Factories*, 12(3). 2013.
Vorobjeva et al., *FEMS Microbiol. Lett.*, 7:261-263, 1980.
Ward, "Proteinases," in Fogarty (ed)., *Microbial Enzymes and Biotechnology. Applied Science*, London, pp 251-317, 1983.
Wells et al., *Nucleic Acids Res.* 11:7911-7925, 1983.
Westers et al., "*Bacillus subtilis* as cell factory for pharmaceutical proteins: a biotechnological approach to optimize the host organism", *Biochimica et Biophysica Acta.*, 1694: 299-310, 2004.
Yang et al, *J. Bacteriol.*, 160: 15-21, 1984.
Yang et al., *Nucleic Acids Res.* 11: 237-249, 1983.
Youngman et al., *Proc. Natl. Acad. Sci. USA* 80: 2305-2309, 1983.

The invention claimed is:

1. A method for introducing a recombinant DNA construct into a modified *Bacillus licheniformis* host cell, the method comprising:
   (a) providing a modified *B. licheniformis* host cell comprising an inactivated genomic diaminopimelate decarboxylase (lysA) gene,
   (b) introducing into the modified cell a recombinant DNA construct comprising a selectable marker encoding a diaminopimelate decarboxylase (LysA) protein,
   (c) cultivating the host cell of step (b) in a growth-medium which does not comprise lysine, and
   (d) selecting a host cell comprising the DNA construct that is capable of growing in the medium of step (c).

2. The method of claim 1, wherein the DNA construct further comprises a downstream (3') nucleic acid sequence encoding a polypeptide of interest (POI), wherein the polynucleotide construct comprises formula (I) or (II) in the 5' to 3' direction:

[5' HR]-[lysA]-[GOI encoding POI]-[3' HR]     (I)

or

[5' HR]-[GOI encoding POI]-[lysA]-[3' HR],    (II)

wherein the 5'-HR and 3'-HR are sufficiently homologous with a genomic region (locus) of the host cell to effect integration into the genome by homologous recombination.

3. A modified *Bacillus licheniformis* host cell produced according to the method of claim 1.

* * * * *

SEQUENCE LISTING

<160> NUMBER OF SEQ ID NOS: 71

<210> SEQ ID NO 1
<211> LENGTH: 1320
<212> TYPE: DNA
<213> ORGANISM: Bacillus licheniformis

<400> SEQUENCE: 1

```
ttgttttac acggtactag cagacaaaat gaaagagggc acctcgaaat cggcggtgtc      60
gatgttctat cattggcaga aagatacgga acacctcttt atgtatacga tgtcgcgctg     120
attagagagc gcgcccgaaa attccagaag gcattcaagg aagccggttt aaaagcgcag     180
gtagcgtatg caagcaaggc gttttcatcg gttgccatga ttcagcttgc cgaacaagag     240
gggctgtctc tggatgtggt atcgggagga gagcttttca ctgcgatcaa agcagggttc     300
ccagctgagc ggattcattt tcacggaaac aataagagcc ctgaagaact agccatggcg     360
ctggagcatc aaatcggctg catcgtgctc gataactttc acgagatcgc cattacagaa     420
gatctttgca agcgatcagg acaaactgta gacgttttgc tcagaatcac tccgggagtt     480
gaagcgcaca cgcacgatta tattacgacg gggcaggaag attccaaatt cggttttgat     540
ctgcataatg gacaggtcga acaagccatc gaacaagtcc tccgctcgtc tgcgtttaag     600
ctcctcggcg tgcactgcca catcggttcg caaattttg atacggcagg atttgtcctt     660
gcagcagaca agattttcga gaagcttgcg gaatggcggg agacttactc tttcattccg     720
gaagtgctca atcttggcgg gggcttcggc atccgctata caaaagacga cgagccgctt     780
```

```
gcagctgatg tttatgttga aaaaatcatc gaggcggtca aagcaaatgc cgagcatttc    840
ggctttgaca tccctgagat ttggatcgaa ccaggccggt ctctcgtcgg tgatgcgggg    900
actacgctgt acacgatcgg ttctcaaaaa gaggtgccgg gcattcgcaa atatgtagcc    960
atcgacggcg gcatgagcga taatatcagg ccggcgcttt atgaggcaaa atatgaagca   1020
gccgtcgcca acaggatgaa cgatgcttgt catgataccg catcaatcgc aggaaaatgc   1080
tgcgaaagcg gagatatgct gatttgggat ttggaaatcc ccgaagttcg cgacggagat   1140
gtgctcgccg tttctgcac cggtgcgtac ggctacagca tggccaacaa ctacaaccgc    1200
attccgcgcc cggccgtcgt ctttgtcgag gacggggaag cgcagctcgt cattcagaga   1260
gagacgtatg aggatatcgt caagctggat ctgccgctga atcgaaagt caaacaataa    1320
```

<210> SEQ ID NO 2
<211> LENGTH: 439
<212> TYPE: PRT
<213> ORGANISM: Bacillus licheniformis

<400> SEQUENCE: 2

```
Met Phe Leu His Gly Thr Ser Arg Gln Asn Glu Arg Gly His Leu Glu
1               5                   10                  15

Ile Gly Gly Val Asp Val Leu Ser Leu Ala Glu Arg Tyr Gly Thr Pro
                20                  25                  30

Leu Tyr Val Tyr Asp Val Ala Leu Ile Arg Glu Arg Ala Arg Lys Phe
            35                  40                  45

Gln Lys Ala Phe Lys Glu Ala Gly Leu Lys Ala Gln Val Ala Tyr Ala
        50                  55                  60

Ser Lys Ala Phe Ser Ser Val Ala Met Ile Gln Leu Ala Glu Gln Glu
65                  70                  75                  80

Gly Leu Ser Leu Asp Val Val Ser Gly Gly Leu Phe Thr Ala Ile
                85                  90                  95

Lys Ala Gly Phe Pro Ala Glu Arg Ile His Phe His Gly Asn Asn Lys
            100                 105                 110

Ser Pro Glu Glu Leu Ala Met Ala Leu Glu His Gln Ile Gly Cys Ile
        115                 120                 125

Val Leu Asp Asn Phe His Glu Ile Ala Ile Thr Glu Asp Leu Cys Lys
130                 135                 140

Arg Ser Gly Gln Thr Val Asp Val Leu Arg Ile Thr Pro Gly Val
145                 150                 155                 160

Glu Ala His Thr His Asp Tyr Ile Thr Thr Gly Gln Glu Asp Ser Lys
                165                 170                 175

Phe Gly Phe Asp Leu His Asn Gly Gln Val Glu Gln Ala Ile Glu Gln
            180                 185                 190

Val Leu Arg Ser Ser Ala Phe Lys Leu Leu Gly Val His Cys His Ile
        195                 200                 205

Gly Ser Gln Ile Phe Asp Thr Ala Gly Phe Val Leu Ala Ala Asp Lys
    210                 215                 220

Ile Phe Glu Lys Leu Ala Glu Trp Arg Glu Thr Tyr Ser Phe Ile Pro
225                 230                 235                 240

Glu Val Leu Asn Leu Gly Gly Gly Phe Gly Ile Arg Tyr Thr Lys Asp
                245                 250                 255

Asp Glu Pro Leu Ala Ala Asp Val Tyr Val Glu Lys Ile Ile Glu Ala
            260                 265                 270

Val Lys Ala Asn Ala Glu His Phe Gly Phe Asp Ile Pro Glu Ile Trp
        275                 280                 285
```

Ile Glu Pro Gly Arg Ser Leu Val Gly Asp Ala Gly Thr Thr Leu Tyr
    290                 295                 300

Thr Ile Gly Ser Gln Lys Glu Val Pro Gly Ile Arg Lys Tyr Val Ala
305                 310                 315                 320

Ile Asp Gly Gly Met Ser Asp Asn Ile Arg Pro Ala Leu Tyr Glu Ala
                325                 330                 335

Lys Tyr Glu Ala Ala Val Ala Asn Arg Met Asn Asp Ala Cys His Asp
            340                 345                 350

Thr Ala Ser Ile Ala Gly Lys Cys Cys Glu Ser Gly Asp Met Leu Ile
        355                 360                 365

Trp Asp Leu Glu Ile Pro Glu Val Arg Asp Gly Asp Val Leu Ala Val
    370                 375                 380

Phe Cys Thr Gly Ala Tyr Gly Tyr Ser Met Ala Asn Asn Tyr Asn Arg
385                 390                 395                 400

Ile Pro Arg Pro Ala Val Val Phe Val Glu Asp Gly Glu Ala Gln Leu
                405                 410                 415

Val Ile Gln Arg Glu Thr Tyr Glu Asp Ile Val Lys Leu Asp Leu Pro
            420                 425                 430

Leu Lys Ser Lys Val Lys Gln
            435

<210> SEQ ID NO 3
<211> LENGTH: 31
<212> TYPE: DNA
<213> ORGANISM: Artificial Sequence
<220> FEATURE:
<223> OTHER INFORMATION: primer sequence

<400> SEQUENCE: 3
gacgcggccg ccgatcaggt cattgcgaac g                                      31

<210> SEQ ID NO 4
<211> LENGTH: 32
<212> TYPE: DNA
<213> ORGANISM: Artificial Sequence
<220> FEATURE:
<223> OTHER INFORMATION: primer sequence

<400> SEQUENCE: 4
tgctcctgca ggcggcttca tgatagtgcg at                                     32

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
ccgcctgcag gagcacgaaa aacacttccc g                                      31

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
atcctcgaga tgggttccgg catacttgt                                         29

```
<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ccaagcgtca tcatcacacc                                                    20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
actcttgcgt tcttctccgt                                                    20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ccaagcgtca tcatcacacc                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cgccgaaaca cctccttttt                                                    20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tttaagcccg acgatcatcc a                                                  21

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
gtgttccgta tctttctgcc aa                                                 22

<210> SEQ ID NO 13
<211> LENGTH: 21
<212> TYPE: DNA
<213> ORGANISM: Artificial Sequence
<220> FEATURE:
<223> OTHER INFORMATION: primer
```

<400> SEQUENCE: 13
ctacagcatg gccaacaact a                                                    21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
atttcagaaa agtcaggcgg g                                                    21

<210> SEQ ID NO 15
<211> LENGTH: 75
<212> TYPE: DNA
<213> ORGANISM: Artificial Sequence
<220> FEATURE:
<223> OTHER INFORMATION: primer

<400> SEQUENCE: 15
gtgatgaaaa ggacccaggt ggcacttttc ggggaaatgt gcgcggaacg ctttgacctt          60
ggcgtacgga aggtc                                                           75

<210> SEQ ID NO 16
<211> LENGTH: 81
<212> TYPE: DNA
<213> ORGANISM: Artificial Sequence
<220> FEATURE:
<223> OTHER INFORMATION: primer

<400> SEQUENCE: 16
ccgaattttt aacaagtacc attttcccta tattttcttc caaaagaaaa gctgaattaa          60
aaatggagac cccctctta g                                                     81

<210> SEQ ID NO 17
<211> LENGTH: 90
<212> TYPE: DNA
<213> ORGANISM: Artificial Sequence
<220> FEATURE:
<223> OTHER INFORMATION: primer

<400> SEQUENCE: 17
ggaagaaaat atagggaaaa tggtacttgt taaaaattcg gaatatttat acaatatcat          60
atgacagaat agtcttttaa gtaagtctac                                           90

<210> SEQ ID NO 18
<211> LENGTH: 74
<212> TYPE: DNA
<213> ORGANISM: Artificial Sequence
<220> FEATURE:
<223> OTHER INFORMATION: primer

<400> SEQUENCE: 18
aaaataaaaa aacggatttc cttcaggaaa tccgtcctct ctgctctttc attgctgcac          60
ccatactgaa actg                                                            74

<210> SEQ ID NO 19
<211> LENGTH: 74
<212> TYPE: DNA
<213> ORGANISM: Artificial Sequence
<220> FEATURE:

```
<223> OTHER INFORMATION: primer

<400> SEQUENCE: 19
gagcagagag gacggatttc ctgaaggaaa tccgtttttt tattttcaag cacgaaaaac    60
acttcccggt gatc                                                      74

<210> SEQ ID NO 20
<211> LENGTH: 73
<212> TYPE: DNA
<213> ORGANISM: Artificial Sequence
<220> FEATURE:
<223> OTHER INFORMATION: primer

<400> SEQUENCE: 20
gtgaaatacc gcacagatgc gtaaggagaa ataccgcat caggaaattg gtacagcaat     60
tctgcctgaa gcc                                                       73

<210> SEQ ID NO 21
<211> LENGTH: 79
<212> TYPE: DNA
<213> ORGANISM: Artificial Sequence
<220> FEATURE:
<223> OTHER INFORMATION: primer

<400> SEQUENCE: 21
gtgatgaaaa ggacccaggt ggcacttttc ggggaaatgt gcgcggaacg ttggggacaa    60
ttgcttgccc agctgaaac                                                 79

<210> SEQ ID NO 22
<211> LENGTH: 57
<212> TYPE: DNA
<213> ORGANISM: Artificial Sequence
<220> FEATURE:
<223> OTHER INFORMATION: primer

<400> SEQUENCE: 22
gagccgaaaa gctgagattt tcgcgactat aatatcttaa catttaatcg tgatgtc       57

<210> SEQ ID NO 23
<211> LENGTH: 57
<212> TYPE: DNA
<213> ORGANISM: Artificial Sequence
<220> FEATURE:
<223> OTHER INFORMATION: primer

<400> SEQUENCE: 23
gacatcacga ttaaatgtta agatattata gtcgcgaaaa tctcagcttt tcggctc       57

<210> SEQ ID NO 24
<211> LENGTH: 81
<212> TYPE: DNA
<213> ORGANISM: Artificial Sequence
<220> FEATURE:
<223> OTHER INFORMATION: primer

<400> SEQUENCE: 24
ccgaattttt aacaagtacc attttcccta tattttcttc caaaagaaaa gctgaattaa    60
aaatggagac ccccctctta g                                              81

<210> SEQ ID NO 25
<211> LENGTH: 70
<212> TYPE: DNA
<213> ORGANISM: Artificial Sequence
```

```
<220> FEATURE:
<223> OTHER INFORMATION: primer

<400> SEQUENCE: 25
gagcagagag gacggatttc ctgaaggaaa tccgtttttt tattttgctt tgagagcggc    60
aacgaagttc                                                           70

<210> SEQ ID NO 26
<211> LENGTH: 76
<212> TYPE: DNA
<213> ORGANISM: Artificial Sequence
<220> FEATURE:
<223> OTHER INFORMATION: primer

<400> SEQUENCE: 26
gtgaaatacc gcacagatgc gtaaggagaa ataccgcat caggaaattg ggccgtattg     60
agcttcggca tctcgg                                                    76

<210> SEQ ID NO 27
<211> LENGTH: 1578
<212> TYPE: DNA
<213> ORGANISM: Bacillus licheniformis

<400> SEQUENCE: 27
atgtttcgag tattggtctc agataaaatg tccagcgacg gcctcaaacc attaatggaa    60
gcagatttta ttgaaattgt agaaagaat gttgcggaag cggaagacga gcttcatacg   120
tttgacgcgc tcttggtgcg gagcgccacg aaggtaaccg aagagctgtt taaaaagatg   180
acttcgctga aaatcgtcgc cagagcaggt gtcggcgtcg acaatatcga tattgacgag   240
gcgacaaaac acggtgttat cgtcgtaaac gcgccaaacg ggaatacaat ttcaaccgct   300
gaacatacct ttgcaatgtt ttcagcgtta atgagacata ttccgcaggc aaacatctcc   360
gtgaaatcaa gggagtggaa tcgttcggct tacgtcggtt cagagcttta cggaaaaacg   420
ctcggcatca tcggaatggg ccgcatcgga agcgaaatcg cgagccgcgc aaaagcattc   480
ggtatgaccg ttcatgtatt tgacccgttc ctgacccaag aaagggcaag caagctcggc   540
gttaacgcga acagctttga agaagttctg gcatgcgccg acatcattac ggttcatacc   600
ccgctcacga agaaacgaa gggacttttg aacaagaaa ccatcgcaaa acgaaaaaa    660 ggcgttcgtc tcgttaactg tgcaagaggc ggcatcatcg atgaagcagc gcttttggaa   720
gctctggaaa gcggacatgt cgctggcgct gccttggatg tattcgaagt cgagcctccg   780
gtcgattcaa aactgatcga tcatccgctt gtagtcgcga ctcctcactt gggcgcctca   840
acaaaagaag cccagctgaa tgtcgctgca caagtgtccg aagaagtcct tcagtatgcg   900
caaggaaacc ctgtgatgtc cgcgatcaac cttccgccca tgacaaagga ttcattcgaa   960 aaatccagc cttatcatca gtttgccaat acgatcggaa accttgtgtc tcagtgcatg  1020
aatgagcctg ttcaagatgt agccatccaa tatgaaggct ccatcgccaa acttgaaacg  1080
tcatttatta cgaaaagcct tttggccgga tttctgaagc cgagggtcgc ggctaccgtt  1140
aacgaagtga atgccggcac cgttgcgaaa gagcgcggca tcagcttcag cgaaaaaatt  1200
tcttccaatg agtcaggcta tgaaaactgc atctctgtga ctgtcacggg agatgtaaca  1260
acattctctt taagagcgac gtacattccg cacttcggcg gacgcatcgt tgccttaaac  1320
ggctttgata ttgattttta tccggctgga caccttgtct acattcacca ccaggataaa  1380
ccaggggcta tcggccatgt cggacgaatt ttaggagacc atgacatcaa tatcgccact  1440
```

-continued

```
atgcaggtag gccgaaaaga aaaggcgga gaagcgatca tgatgctttc ctttgaccgc    1500
caccttgagg acgatatttt agctgagctg aaaaacatcc cggatatcgt gtctgttaaa   1560
gccatcgacc ttccttaa                                                  1578
```

<210> SEQ ID NO 28
<211> LENGTH: 525
<212> TYPE: PRT
<213> ORGANISM: Bacillus licheniformis

<400> SEQUENCE: 28

```
Met Phe Arg Val Leu Val Ser Asp Lys Met Ser Asp Gly Leu Lys
1               5                   10                  15

Pro Leu Met Glu Ala Asp Phe Ile Glu Ile Val Glu Lys Asn Val Ala
            20                  25                  30

Glu Ala Glu Asp Glu Leu His Thr Phe Asp Ala Leu Leu Val Arg Ser
        35                  40                  45

Ala Thr Lys Val Thr Glu Glu Leu Phe Lys Lys Met Thr Ser Leu Lys
    50                  55                  60

Ile Val Ala Arg Ala Gly Val Gly Val Asp Asn Ile Asp Ile Asp Glu
65                  70                  75                  80

Ala Thr Lys His Gly Val Ile Val Val Asn Ala Pro Asn Gly Asn Thr
                85                  90                  95

Ile Ser Thr Ala Glu His Thr Phe Ala Met Phe Ser Ala Leu Met Arg
            100                 105                 110

His Ile Pro Gln Ala Asn Ile Ser Val Lys Ser Arg Glu Trp Asn Arg
        115                 120                 125

Ser Ala Tyr Val Gly Ser Glu Leu Tyr Gly Lys Thr Leu Gly Ile Ile
    130                 135                 140

Gly Met Gly Arg Ile Gly Ser Glu Ile Ala Ser Arg Ala Lys Ala Phe
145                 150                 155                 160

Gly Met Thr Val His Val Phe Asp Pro Phe Leu Thr Gln Glu Arg Ala
                165                 170                 175

Ser Lys Leu Gly Val Asn Ala Asn Ser Phe Glu Glu Val Leu Ala Cys
            180                 185                 190

Ala Asp Ile Ile Thr Val His Thr Pro Leu Thr Lys Glu Thr Lys Gly
        195                 200                 205

Leu Leu Asn Lys Glu Thr Ile Ala Lys Thr Lys Lys Gly Val Arg Leu
    210                 215                 220

Val Asn Cys Ala Arg Gly Gly Ile Ile Asp Glu Ala Ala Leu Leu Glu
225                 230                 235                 240

Ala Leu Glu Ser Gly His Val Ala Gly Ala Ala Leu Asp Val Phe Glu
                245                 250                 255

Val Glu Pro Pro Val Asp Ser Lys Leu Ile Asp His Pro Leu Val Val
            260                 265                 270

Ala Thr Pro His Leu Gly Ala Ser Thr Lys Glu Ala Gln Leu Asn Val
        275                 280                 285

Ala Ala Gln Val Ser Glu Glu Val Leu Gln Tyr Ala Gln Gly Asn Pro
    290                 295                 300

Val Met Ser Ala Ile Asn Leu Pro Ala Met Thr Lys Asp Ser Phe Glu
305                 310                 315                 320

Lys Ile Gln Pro Tyr His Gln Phe Ala Asn Thr Ile Gly Asn Leu Val
                325                 330                 335

Ser Gln Cys Met Asn Glu Pro Val Gln Asp Val Ala Ile Gln Tyr Glu
            340                 345                 350
```

Gly Ser Ile Ala Lys Leu Glu Thr Ser Phe Ile Thr Lys Ser Leu Leu
        355                 360                 365

Ala Gly Phe Leu Lys Pro Arg Val Ala Ala Thr Val Asn Glu Val Asn
370                 375                 380

Ala Gly Thr Val Ala Lys Glu Arg Gly Ile Ser Phe Ser Glu Lys Ile
385                 390                 395                 400

Ser Ser Asn Glu Ser Gly Tyr Glu Asn Cys Ile Ser Val Thr Val Thr
                405                 410                 415

Gly Asp Val Thr Thr Phe Ser Leu Arg Ala Thr Tyr Ile Pro His Phe
            420                 425                 430

Gly Gly Arg Ile Val Ala Leu Asn Gly Phe Asp Ile Asp Phe Tyr Pro
        435                 440                 445

Ala Gly His Leu Val Tyr Ile His His Gln Asp Lys Pro Gly Ala Ile
    450                 455                 460

Gly His Val Gly Arg Ile Leu Gly Asp His Asp Ile Asn Ile Ala Thr
465                 470                 475                 480

Met Gln Val Gly Arg Lys Glu Lys Gly Gly Glu Ala Ile Met Met Leu
                485                 490                 495

Ser Phe Asp Arg His Leu Glu Asp Ile Leu Ala Glu Leu Lys Asn
            500                 505                 510

Ile Pro Asp Ile Val Ser Val Lys Ala Ile Asp Leu Pro
        515                 520                 525

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
tacagcattt cgcggccgta c                                           21

<210> SEQ ID NO 30
<211> LENGTH: 56
<212> TYPE: DNA
<213> ORGANISM: Artificial Sequence
<220> FEATURE:
<223> OTHER INFORMATION: primer

<400> SEQUENCE: 30
catagatcgg ggtgaagatg tcatgatctt attttgcctc ataaagcgcc ggcctg     56

<210> SEQ ID NO 31
<211> LENGTH: 56
<212> TYPE: DNA
<213> ORGANISM: Artificial Sequence
<220> FEATURE:
<223> OTHER INFORMATION: primer

<400> SEQUENCE: 31
caggccggcg ctttatgagg caaaataaga tcatgacatc ttcaccccga tctatg     56

<210> SEQ ID NO 32
<211> LENGTH: 52
<212> TYPE: DNA
<213> ORGANISM: Artificial Sequence
<220> FEATURE:
<223> OTHER INFORMATION: primer

<400> SEQUENCE: 32

```
attagcccgg tcgctgttct atgcatttaa gagacccgct aagaagtaca ta        52

<210> SEQ ID NO 33
<211> LENGTH: 52
<212> TYPE: DNA
<213> ORGANISM: Artificial Sequence
<220> FEATURE:
<223> OTHER INFORMATION: primer

<400> SEQUENCE: 33
tatgtacttc ttagcgggtc tcttaaatgc atagaacagc gaccgggcta at        52

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
gttcagacac acaatatcag cag                                        23

<210> SEQ ID NO 35
<211> LENGTH: 52
<212> TYPE: DNA
<213> ORGANISM: Artificial Sequence
<220> FEATURE:
<223> OTHER INFORMATION: primer

<400> SEQUENCE: 35
ggaaatgtgc gcggaacccc tatttgcatt tcgcggccgt acgggtcaat cg        52

<210> SEQ ID NO 36
<211> LENGTH: 52
<212> TYPE: DNA
<213> ORGANISM: Artificial Sequence
<220> FEATURE:
<223> OTHER INFORMATION: primer

<400> SEQUENCE: 36
atactgacat agatcggggt gaagatgtca tgatcttttt aacaaaaaac ac        52

<210> SEQ ID NO 37
<211> LENGTH: 52
<212> TYPE: DNA
<213> ORGANISM: Artificial Sequence
<220> FEATURE:
<223> OTHER INFORMATION: primer

<400> SEQUENCE: 37
gtgttttttg ttaaaaagat catgacatct tcacccgat ctatgtcagt at         52

<210> SEQ ID NO 38
<211> LENGTH: 52
<212> TYPE: DNA
<213> ORGANISM: Artificial Sequence
<220> FEATURE:
<223> OTHER INFORMATION: primer

<400> SEQUENCE: 38
attagcccgg tcgctgttct atgcatttaa gagacccgct aagaagtaca ta        52

<210> SEQ ID NO 39
<211> LENGTH: 52
<212> TYPE: DNA
```

<213> ORGANISM: Artificial Sequence
<220> FEATURE:
<223> OTHER INFORMATION: primer

<400> SEQUENCE: 39
tatgtacttc ttagcgggtc tcttaaatgc atagaacagc gaccgggcta at    52

<210> SEQ ID NO 40
<211> LENGTH: 52
<212> TYPE: DNA
<213> ORGANISM: Artificial Sequence
<220> FEATURE:
<223> OTHER INFORMATION: primer

<400> SEQUENCE: 40
agatgcgtaa ggagaaaata ccgcatggag ggcatttgac ttgaagagaa aa    52

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
gtcaatcgtt gacgaatgaa gg    22

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
ggcatttgac ttgaagagaa aattctc    27

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
gatgcggccg catcgaaacg gccatcacaa g    31

<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
ggatgtcctg cagggtcaat gagtttcacg cggaa    35

<210> SEQ ID NO 45
<211> LENGTH: 34
<212> TYPE: DNA
<213> ORGANISM: Artificial Sequence
<220> FEATURE:
<223> OTHER INFORMATION: primer

<400> SEQUENCE: 45
attgaccctg caggacatcc cggatatcgt gtct    34

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46
atgctcgagc ggaagcctca gagtggatt                                        29

<210> SEQ ID NO 47
<211> LENGTH: 52
<212> TYPE: DNA
<213> ORGANISM: Artificial Sequence
<220> FEATURE:
<223> OTHER INFORMATION: primer

<400> SEQUENCE: 47
cggggaaatg tgcgcggaac ccctatttgc tctgaccaaa gactcctgct tc             52

<210> SEQ ID NO 48
<211> LENGTH: 51
<212> TYPE: DNA
<213> ORGANISM: Artificial Sequence
<220> FEATURE:
<223> OTHER INFORMATION: primer

<400> SEQUENCE: 48
gtcagctgtt tatcagcgag agctcggaaa aagtgagttt accgaaatat c              51

<210> SEQ ID NO 49
<211> LENGTH: 52
<212> TYPE: DNA
<213> ORGANISM: Artificial Sequence
<220> FEATURE:
<223> OTHER INFORMATION: primer

<400> SEQUENCE: 49
catattccgc attcgcaatg cctaccgcat actaaaaacc gcacattcac ag             52

<210> SEQ ID NO 50
<211> LENGTH: 52
<212> TYPE: DNA
<213> ORGANISM: Artificial Sequence
<220> FEATURE:
<223> OTHER INFORMATION: primer

<400> SEQUENCE: 50
cagatgcgta aggagaaaat accgcatatg ctgatcactc cccagttaat cg             52

<210> SEQ ID NO 51
<211> LENGTH: 51
<212> TYPE: DNA
<213> ORGANISM: Artificial Sequence
<220> FEATURE:
<223> OTHER INFORMATION: primer

<400> SEQUENCE: 51
gatatttcgg taaactcact ttttccgagc tctcgctgat aaacagctga c              51

<210> SEQ ID NO 52
<211> LENGTH: 52
<212> TYPE: DNA
<213> ORGANISM: Artificial Sequence
<220> FEATURE:

<223> OTHER INFORMATION: primer

<400> SEQUENCE: 52
ctgtgaatgt gcggttttta gtatgcggta ggcattgcga atgcggaata tg         52

<210> SEQ ID NO 53
<211> LENGTH: 22
<212> TYPE: DNA
<213> ORGANISM: Artificial Sequence
<220> FEATURE:
<223> OTHER INFORMATION: primer

<400> SEQUENCE: 53
gcttcaatcg ttgaacgctg gc                                          22

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
cagttaatcg aacagatcag atctc                                       25

<210> SEQ ID NO 55
<211> LENGTH: 52
<212> TYPE: DNA
<213> ORGANISM: Artificial Sequence
<220> FEATURE:
<223> OTHER INFORMATION: primer

<400> SEQUENCE: 55
ggaaatgtgc gcggaacccc tatttggtct atgtgaagct gtcgccgaac gt         52

<210> SEQ ID NO 56
<211> LENGTH: 52
<212> TYPE: DNA
<213> ORGANISM: Artificial Sequence
<220> FEATURE:
<223> OTHER INFORMATION: primer

<400> SEQUENCE: 56
aacaatatgg cccgtttgtt gaactgggat taataaaaaa taaaaataat cc         52

<210> SEQ ID NO 57
<211> LENGTH: 52
<212> TYPE: DNA
<213> ORGANISM: Artificial Sequence
<220> FEATURE:
<223> OTHER INFORMATION: primer

<400> SEQUENCE: 57
ggattatttt tatttttat taatcccagt tcaacaaacg ggccatattg tt          52

<210> SEQ ID NO 58
<211> LENGTH: 52
<212> TYPE: DNA
<213> ORGANISM: Artificial Sequence
<220> FEATURE:
<223> OTHER INFORMATION: primer

<400> SEQUENCE: 58
taaaagtcaa cccgactttt tttatagccg cgcataaaaa aagaccattc ct         52

```
<210> SEQ ID NO 59
<211> LENGTH: 52
<212> TYPE: DNA
<213> ORGANISM: Artificial Sequence
<220> FEATURE:
<223> OTHER INFORMATION: primer

<400> SEQUENCE: 59
aggaatggtc tttttttatg cgcggctata aaaaaagtcg ggttgacttt ta          52

<210> SEQ ID NO 60
<211> LENGTH: 52
<212> TYPE: DNA
<213> ORGANISM: Artificial Sequence
<220> FEATURE:
<223> OTHER INFORMATION: primer

<400> SEQUENCE: 60
agatgcgtaa ggagaaaata ccgcatgact catctcctta ctcgtgtaat cc          52

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
cattaccgac atcgctcttg c                                            21

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ctccttactc gtgtaatccg cattc                                        25

<210> SEQ ID NO 63
<211> LENGTH: 22
<212> TYPE: DNA
<213> ORGANISM: Artificial Sequence
<220> FEATURE:
<223> OTHER INFORMATION: primer

<400> SEQUENCE: 63
gcttcaatcg ttgaacgctg gc                                           22

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
ctgacggaaa attggtgcag ac                                           22

<210> SEQ ID NO 65
<211> LENGTH: 720
<212> TYPE: DNA
<213> ORGANISM: Bacillus licheniformis

<400> SEQUENCE: 65
```

```
atgaacaata cgccgcccat catcgcgctt gattttgcat cagcacagga acatatgcg    60 tttttggacc ggtttcaagg agaagagctg ttcgttaagg tgggcatgga gcttttttat  120
caggaaggac ctgccatcct tgaaaatctg caggagcgcg gctgccgcat tttcctcgat  180
ctaaagtgcc acgacattcc aacgaccgta tacaaggcga tgaaaaggct ggcgggattt  240
ggcgtcagtc ttgtcaatgt gcacgcagca ggcggaaagc aaatgatgga gtcggcgctt  300
gaaggccttg aagcggggac tccggcaggc caaaaacgcc cttcattaat tgccgtgact  360
cagctgacaa gcacgtcctc agaaatgctt cagcgtgagc tcctgattga aacgccgctt  420
ctcgatacag ttgtccacta cagccggctg gctgaagaaa gcggtcttga cggcgtcgtc  480
tgctccgttc atgaagccga acacatttac cgggctgtgt ctgtagattt tctgaccgtg  540
acacccggaa ttcgcatggc agatgacaaa aacaacgacc aggtccgggt ggcgacgcct  600
ggctacgcaa gggaaaaagg cgtgtcggcg atcgttgtcg ccgttcgat acccaggcg    660 gaagatcctg tgtcagccta cagaagaata ggacatgagt gggagggaac caaggcatga  720
```

<210> SEQ ID NO 66
<211> LENGTH: 239
<212> TYPE: PRT
<213> ORGANISM: Bacillus licheniformis

<400> SEQUENCE: 66

Met Asn Asn Thr Pro Pro Ile Ile Ala Leu Asp Phe Ala Ser Ala Gln
1               5                   10                  15

Glu Thr Tyr Ala Phe Leu Asp Arg Phe Gln Gly Glu Glu Leu Phe Val
            20                  25                  30

Lys Val Gly Met Glu Leu Phe Tyr Gln Glu Gly Pro Ala Ile Leu Glu
        35                  40                  45

Asn Leu Gln Glu Arg Gly Cys Arg Ile Phe Leu Asp Leu Lys Cys His
    50                  55                  60

Asp Ile Pro Thr Thr Val Tyr Lys Ala Met Lys Arg Leu Ala Gly Phe
65                  70                  75                  80

Gly Val Ser Leu Val Asn Val His Ala Ala Gly Gly Lys Gln Met Met
                85                  90                  95

Glu Ser Ala Leu Glu Gly Leu Glu Ala Gly Thr Pro Ala Gly Gln Lys
            100                 105                 110

Arg Pro Ser Leu Ile Ala Val Thr Gln Leu Thr Ser Thr Ser Ser Glu
        115                 120                 125

Met Leu Gln Arg Glu Leu Leu Ile Glu Thr Pro Leu Leu Asp Thr Val
    130                 135                 140

Val His Tyr Ser Arg Leu Ala Glu Glu Ser Gly Leu Asp Gly Val Val
145                 150                 155                 160

Cys Ser Val His Glu Ala Glu His Ile Tyr Arg Ala Val Ser Val Asp
                165                 170                 175

Phe Leu Thr Val Thr Pro Gly Ile Arg Met Ala Asp Asp Lys Asn Asn
            180                 185                 190

Asp Gln Val Arg Val Ala Thr Pro Gly Tyr Ala Arg Glu Lys Gly Val
        195                 200                 205

Ser Ala Ile Val Val Gly Arg Ser Ile Thr Gln Ala Glu Asp Pro Val
    210                 215                 220

Ser Ala Tyr Arg Arg Ile Gly His Glu Trp Glu Gly Thr Lys Ala
225                 230                 235

<210> SEQ ID NO 67

<211> LENGTH: 579
<212> TYPE: DNA
<213> ORGANISM: Artificial Sequence
<220> FEATURE:
<223> OTHER INFORMATION: encodes comK protein

<400> SEQUENCE: 67

```
atgagcacag aggatatgac aaaggatacg tatgaagtaa acagttcgac aatggctgtc      60
ctgcctctgg gtgaggggga gaaatccgcc tcaaaaatac ttgagaccga caggactttc     120
cgcgtcaata tgaagccgtt tcaaattatc gaaagaagct gccgctattt cggatcgagc     180
tatgcgggaa gaaaagcggg cacatatgaa gtcattaaag tttcccataa accgccgatc     240
atggtggatc actcaaacaa catttttctt ttccccacat tttcctcaac tcgtcctcag     300
tgcgggtggc tttcccatgc gcatgttcac gagttttgcg cggcaaagta tgacaacacg     360
tttgtcacgt ttgtcaacgg ggaaacgctg gagctgcccg tatccatctc atctttcgaa     420
aaccaggttt accgaacggc atggctgaga acaaaattta tcgacaggat tgaaggaaac     480
cccatgcaga gaaacagga atttatgctc tatccgaaag aagaccggaa tcagctgata     540
tacgaattca tcctcaggga gctgaaaaag cgctattga                            579
```

<210> SEQ ID NO 68
<211> LENGTH: 192
<212> TYPE: PRT
<213> ORGANISM: Artificial Sequence
<220> FEATURE:
<223> OTHER INFORMATION: comK protein

<400> SEQUENCE: 68

```
Met Ser Thr Glu Asp Met Thr Lys Asp Thr Tyr Glu Val Asn Ser Ser
1               5                   10                  15
Thr Met Ala Val Leu Pro Leu Gly Glu Gly Glu Lys Ser Ala Ser Lys
            20                  25                  30
Ile Leu Glu Thr Asp Arg Thr Phe Arg Val Asn Met Lys Pro Phe Gln
        35                  40                  45
Ile Ile Glu Arg Ser Cys Arg Tyr Phe Gly Ser Ser Tyr Ala Gly Arg
    50                  55                  60
Lys Ala Gly Thr Tyr Glu Val Ile Lys Val Ser His Lys Pro Pro Ile
65                  70                  75                  80
Met Val Asp His Ser Asn Asn Ile Phe Leu Phe Pro Thr Phe Ser Ser
                85                  90                  95
Thr Arg Pro Gln Cys Gly Trp Leu Ser His Ala His Val His Glu Phe
            100                 105                 110
Cys Ala Ala Lys Tyr Asp Asn Thr Phe Val Thr Phe Val Asn Gly Glu
        115                 120                 125
Thr Leu Glu Leu Pro Val Ser Ile Ser Ser Phe Glu Asn Gln Val Tyr
    130                 135                 140
Arg Thr Ala Trp Leu Arg Thr Lys Phe Ile Asp Arg Ile Glu Gly Asn
145                 150                 155                 160
Pro Met Gln Lys Lys Gln Glu Phe Met Leu Tyr Pro Lys Glu Asp Arg
                165                 170                 175
Asn Gln Leu Ile Tyr Glu Phe Ile Leu Arg Glu Leu Lys Lys Arg Tyr
            180                 185                 190
```

<210> SEQ ID NO 69
<211> LENGTH: 1625
<212> TYPE: DNA
<213> ORGANISM: Artificial Sequence
<220> FEATURE:
<223> OTHER INFORMATION: tetracycline gene

<400> SEQUENCE: 69

```
gttcaacaaa cgggccatat tgttgtataa gtgatgaaat actgaattta aaacttagtt    60
tatatgtggt aaaatgtttt aatcaagttt aggaggaatt aattatgaag tgtaatgaat   120
gtaacagggt tcaattaaaa gagggaagcg tatcattaac cctataaact acgtctgccc   180
tcattattgg agggtgaaat gtgaatacat cctattcaca atcgaattta cgacacaacc   240
aaattttaat ttggctttgc attttatctt ttttagcgt attaaatgaa atggttttga    300
acgtctcatt acctgatatt gcaaatgatt taataaaacc acctgcgagt acaaactggg   360
tgaacacagc ctttatgtta acctttccca ttggaacagc tgtatatgga aagctatctg   420
atcaattagg catcaaaagg ttactcctat tggaattat aataaattgt ttcgggtcgg    480
taattgggtt tgttggccat tctttctttt ccttacttat tatggctcgt tttattcaag   540
gggctggtgc agctgcattt ccagcactcg taatggttgt agttgcgcgc tatattccaa   600
aggaaaatag gggtaaagca tttggtctta ttggatcgat agtagccatg ggagaaggag   660
tcggtccagc gattggtgga atgatagccc attatattca ttggtcctat cttctactca   720
ttcctatgat aacaattatc actgttccgt ttcttatgaa attattaaag aaagaagtaa   780
ggataaaagg tcattttgat atcaaaggaa ttatactaat gtctgtaggc attgtatttt   840
ttatgttgtt tacaacatca tatagcattt cttttcttat cgttagcgtg ctgtcattcc   900
tgatatttgt aaaacatatc aggaaagtaa cagatccttt tgttgatccc ggattaggga   960
aaaatatacc ttttatgatt ggagttcttt gtggggaat tatatttgga acagtagcag   1020
ggtttgtctc tatggttcct tatatgatga agatgttca ccagctaagt actgccgaaa   1080
tcggaagtgt aattattttc cctggaacaa tgagtgtcat tattttcggc tacattggtg   1140
ggatacttgt tgatagaaga ggtccttttat acgtgttaaa catcggagtt acatttcttt   1200
ctgttagctt tttaactgct tccttttctt tagaaacaac atcatggttc atgacaatta   1260
taatcgtatt tgttttaggt gggctttcgt tcaccaaaac agttatatca acaattgttt   1320
caagtagctt gaaacagcag gaagctggtg ctggaatgag tttgcttaac tttaccagct   1380
ttttatcaga gggaacaggt attgcaattg taggtggttt attatccata cccttacttg   1440
atcaaaggtt gttacctatg gaagttgatc agtcaactta tctgtatagt aatttgttat   1500
tactttttc aggaatcatt gtcattagtt ggctggttac cttgaatgta tataaacatt   1560
ctcaaaggga tttctaaata tgatgaagaa agaccattcc aatcaggaat ggtctttttt   1620
tatgc                                                              1625
```

<210> SEQ ID NO 70
<211> LENGTH: 21
<212> TYPE: DNA
<213> ORGANISM: Artificial Sequence
<220> FEATURE:
<223> OTHER INFORMATION: primer

<400> SEQUENCE: 70

```
tgccctctcta ttctgaaacc g                                            21
```

<210> SEQ ID NO 71
<211> LENGTH: 22
<212> TYPE: DNA
<213> ORGANISM: Artificial Sequence
<220> FEATURE:

```
<223> OTHER INFORMATION: primer

<400> SEQUENCE: 71
accttccttt atgctttcga cg                                              22
```